United States Patent
Clark

(10) Patent No.: US 7,157,475 B2
(45) Date of Patent: Jan. 2, 2007

(54) DIAMIDE INVERTEBRATE PEST CONTROL AGENTS

(75) Inventor: David Alan Clark, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 165 days.

(21) Appl. No.: 10/496,732

(22) PCT Filed: Jan. 13, 2003

(86) PCT No.: PCT/US03/00917

§ 371 (c)(1),
(2), (4) Date: May 21, 2004

(87) PCT Pub. No.: WO03/062221

PCT Pub. Date: Jul. 31, 2003

(65) Prior Publication Data

US 2004/0259913 A1    Dec. 23, 2004

Related U.S. Application Data

(60) Provisional application No. 60/350,587, filed on Jan. 22, 2002.

(51) Int. Cl.
*A61K 31/4439* (2006.01)
*A61K 31/415* (2006.01)
*C07D 231/12* (2006.01)
*C07D 401/04* (2006.01)

(52) U.S. Cl. ............... 514/341; 514/406; 546/14; 546/275.4; 548/110; 548/374.1

(58) Field of Classification Search ............... None
See application file for complete search history.

(56) References Cited

U.S. PATENT DOCUMENTS

2004/0138450 A1    7/2004    Clark

FOREIGN PATENT DOCUMENTS

WO    WO 00/34729    *    6/2000
WO    WO 01/70671 A       9/2001

OTHER PUBLICATIONS

Teegarden et al., STN International (2006) HCAPLUS Database, Accession No. 2000:441762.*
XP004027153—Suto M J et al, "Synthesis of Boxazomyci B and Related Analogs" Tetrahedron Letters, Elsevier Science Publishers, Amsterdam, NL, vol. 36, No. 40, Oct. 2, 1995, pp. 7213-7216.

XP002242112—Skaric, Vinko et al, "Conversion of stereoisomeric 2-amino-1-carbamoylcyclohexane-5, 5-dicarboxylates into 6-amino-3-azabicyclo '3.3.1 nona-2,4-dione-1-carboxylates" Canadian Journal of Chemistry (1980), 58(17), 1860-4.
XP002242113—Docken, James S. et al., "Vinylogous system. 4. Mass spectra of vinylogous ureas and ureides" Journal of Organic Chemistry (1978), 43(3), 505-9.
XP002242114—Nohira, Hiroyuki et al., "Synthesis and reaction of optically active 2-aryl-cis-and trans-hexahydro-3, 1, 4-benzoxazones" Retrieved from STN Database Accession No. 88:50752, 1977.
XP-002242115—Kato, Tetsuzo et al., "Synthesis of 3-amino-4-methyl-2-pentenamide, 2-amino-1-clohexene-1-carboxamide, 3-amino-2, 4-diphenyl-2-butenamide, and sythesis of 4(3H)-pyrimidone derivatives from them" retrienved from STN Database accession No. 75:151753, 1971.

* cited by examiner

Primary Examiner—Joseph K. McKane
Assistant Examiner—Andrew B. Freistein

(57) ABSTRACT

Compounds of Formula (I), and their N-oxides and suitable slats, are disclosed which are useful as invertebrate pest control agents, wherein A and B are independently O or S; E is C or N; J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$; K is taken together with the two contiguous linking carbon atoms to form a 5- or 6-membered nanoaromatic carbocyclic or heterocyclic ring optionally including one or two ring members selected from the group consisting of C(=O), SO or S(O)$_2$, each ring optionally substituted with 1 to 4 $R^4$; and $R^1$, $R^2$, $R^3$, $R^4$ and $R^5$ are as defined in the disclosure. Also disclosed are compositions containing the compounds of Formula (I) and a method for controlling an invertebrate pests which involves contacting the pest or its environment with an effective amount of a compound of Formula (I)

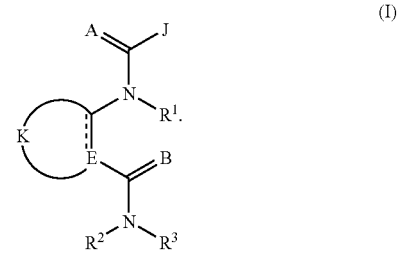

14 Claims, No Drawings

DIAMIDE INVERTEBRATE PEST CONTROL AGENTS

CROSS-REFERENCE TO RELATED APPLICATIONS

This application is a national filing under 35 U.S.C. 371 of International Application No. PCT/US03/00917, filed 13 Jan. 2003, which claims priority benefit of Provisional Application 60/350,587, filed 22 Jan. 2002.

FIELD OF THE INVENTION

This invention relates to certain diamides, their N-oxides, suitable salts and compositions thereof, and a method of use for controlling invertebrate pests in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

WO01/070671 discloses N-acyl anthranilic acid derivatives of Formula i as arthropodicides

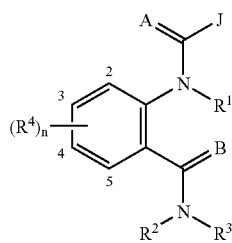

wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$–$C_6$ alkyl; $R^2$ is H or $C_1$–$C_6$ alkyl; each $R^4$ is independently H, $C_1$–$C_6$ alky, $C_1$–$C_6$ haloalkyl, halogen or CN; and n is 1 to 4.

SUMMARY OF THE INVENTION

This invention provides compounds of Formula I, their N-oxides and suitable salts thereof

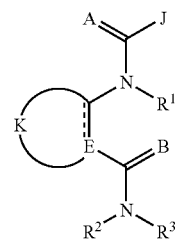

wherein
- A and B are independently O or S;
- E is C or N;
- J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;
- K is taken together with the two contiguous linking atoms to form a 5- or 6-membered nonaromatic carbocyclic or heterocyclic ring optionally including one or two ring members selected from the group consisting of C(=O), SO and S(O)$_2$, each ring optionally substituted with 1 to 4 $R^4$;
- $R^1$ and $R^2$ are each independently H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;
- $R^3$ is H; G; $C_1$–$C_6$ alkyl, $C_2$–$C_6$ alkenyl, $C_2$–$C_6$ alkynyl, $C_3$–$C_6$ cycloalkyl, each optionally substituted with 1 to 5 substituents selected from the group consisting of G, halogen, CN, NO$_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, phenyl, phenoxy and 5- or 6-membered heteroaromatic ring, each phenyl, phenoxy and 5- or 6-membered heteroaromatic ring optionally substituted with one to three substituents independently selected from $R^6$; or phenyl optionally substituted with 1 to 3 $R^6$; or
- $R^2$ and $R^3$ can be taken together with the nitrogen to which they are attached to form a ring containing 2 to 6 atoms of carbon and optionally one additional atom of nitrogen, sulfur or oxygen, and said ring optionally substituted with one to four substituents independently selected from $R^{12}$; and
- G is a 5- or 6-membered nonaromatic carbocyclic or heterocyclic ring, optionally including one or two ring members selected from the group consisting of C(=O), SO and S(O)$_2$ and optionally substituted with one to four substituents selected from $R^{12}$;
- each $R^4$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, NO$_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_1$–$C_4$ alkoxyalkyl, $C_1$–$C_4$ hydroxyalkyl, C(O)$R^{10}$, $CO_2R^{10}$, C(O)$NR^{10}R^{11}$, $NR^{10}R^{11}$, N($R^{11}$)$CO_2R^{10}$ or $C_3$–$C_6$ trialkylsilyl; or each $R^4$ is independently a phenyl, benzyl, phenoxy or 5- or 6-membered heteroaromatic ring, each ring optionally substituted with one to three substituents independently selected from $R^6$;

each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylsulfonyloxy, $C_1$–$C_4$ haloalkylthio, $C_1$–$C_4$ haloalkylsulfinyl, $C_1$–$C_4$ haloalkylsulfonyl, $C_1$–$C_4$ haloalkylsulfonyloxy, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring or ring system optionally substituted with one to three substituents independently selected from $R^6$; or two $R^5$ groups when attached to adjacent carbon atoms can be taken together as —$OCF_2O$—, —$CF_2CF_2O$— or —$OCF_2CF_2O$—;

each $R^6$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^{10}$ is independently H, $C_1$–$C_4$ alkyl or $C_1$–$C_4$ haloalkyl;

each $R^{11}$ is independently H or $C_1$–$C_4$ alkyl; and each $R^{12}$ is independently $C_1$–$C_2$ alkyl, halogen, CN, $NO_2$ or $C_1$–$C_2$ alkoxy.

This invention also provides a method for controlling an invertebrate pest comprising contacting the invertebrate pest or its environment with a biologically effective amount of a compound of Formula I, an N-oxide thereof or a suitable salt of the compound (e.g., as a composition described herein). This invention also relates to such a method wherein the invertebrate pest or its environment is contacted with a biologically effective amount of a compound of Formula I or a composition comprising a compound of Formula I, an N-oxide thereof or a suitable salt of the compound and a biologically effective amount of at least one additional compound or agent for controlling invertebrate pests.

This invention also provides a composition for controlling an invertebrate pest comprising a biologically effective amount of a compound of Formula I, an N-oxide thereof or a suitable salt of the compound and at least one additional component selected from the group consisting of surfactants, solid diluents and liquid diluents. This invention also provides a composition comprising a biologically effective amount of a compound of Formula I, an N-oxide thereof or a suitable salt of the compound and an effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. Examples of "alkylsulfonyloxy" include $CH_3S(O)_2O$, $CH_3CH_2S(O)_2O$, $CH_3CH_2CH_2S(O)_2O$, $(CH_3)_2CHS(O)_2O$ and the different butylsulfonyloxy, pentylsulfonyloxy and hexylsulfonyloxy isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl.

"Aromatic" indicates that each of the ring atoms is essentially in the same plane and has a p-orbital perpendicular to the ring plane, and in which (4n+2) π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. The term "aromatic carbocyclic ring or ring system" includes fully aromatic carbocycles and carbocycles in which at least one ring of a polycyclic ring system is aromatic (e.g. phenyl and naphthyl). The term "nonaromatic carbocyclic ring or ring system" denotes fully saturated carbocycles as well as partially or fully unsaturated carbocycles where the Hückel rule is not satisfied by any of the rings in the ring system. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The term "heteroaromatic ring or ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkylsulfonyloxy" include $CF_3S(O)_2O$, $CCl_3S(O)_2O$, $CF_3CH_2S(O)_2O$ and $CF_3CF_2S(O)_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH3)C(=O)$.

The total number of carbon atoms in a substituent group is indicated by the "$C_i$–$C_j$" prefix where i and j are numbers from 1 to 6. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted with one to three substituents" and the like indicates that one to three of the available positions on the group may be substituted. When a group contains a substituent which can be hydrogen, for example $R^1$ or $R^3$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic and valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$. The term "optionally substituted" in connection with these J groups refers to groups which are unsubstituted or have at least one non-hydrogen substituent that does not extinguish the biological activity possessed by the unsubstituted analog. An example of phenyl optionally substituted with 1 to 4 $R^5$ is the ring illustrated as U-1 in Exhibit 1, wherein $R^v$ is $R^5$ and r is an integer from 0 to 4. An example of a naphthyl group optionally substituted with 1 to 4 $R^5$ is illustrated as U-85 in Exhibit 1, wherein $R^v$ is $R^5$ and r is an integer from 0 to 4. Examples of 5- or 6-membered heteroaromatic rings optionally substituted with 1 to 4 $R^5$ include the rings U-2 through U-53 illustrated in Exhibit 1 wherein $R^v$ is $R^5$ and r is an integer from 0 to 4. Note that J-1 through J-13 below also denote 5- or 6-membered heteroaromatic rings. Note that U-2 through U-20 are examples of J-1, U-21 through U-35 and U-40 are examples of J-2, U-36 through U-39 are examples of J-3, U-41 through U-48 are examples of J-4 and U-49 through U-53 are examples of J-5. Note that U-11 is equivalent to J-6, U-26 is equivalent to J-7 or J-10, U-42 is equivalent to J-8, U-45 is equivalent to J-9, U-4 is equivalent to J-11 and U-24 is equivalent to J-12 or J-13. Also note that in J-6 through J-13 that $R^7$ and $R^9$ are subsets of $R^5$ as defined in the Summary of the Invention. Examples of aromatic 8-, 9- or 10-membered fused heterobicyclic ring systems optionally substituted with 1 to 4 $R^5$ include U-54 through U-84 illustrated in Exhibit 1 wherein $R^v$ is $R^5$ and r is an integer from 0 to 4.

The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon or nitrogen of the U group. Note that when the attachment point on the U group is illustrated as floating, the U group can be attached to the remainder of Formula I through any available carbon or nitrogen of the U group by replacement of a hydrogen atom.

Exhibit 1

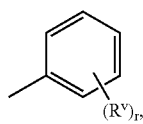
U-1

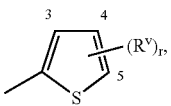
U-2

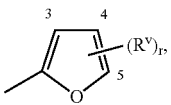
U-3

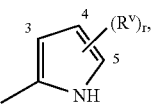
U-4

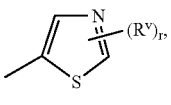
U-5

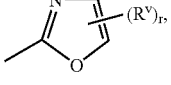
U-6

-continued

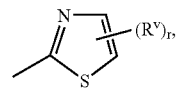
U-7

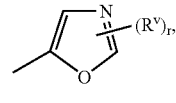
U-8

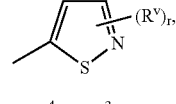
U-9

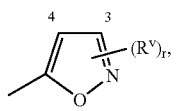
U-10

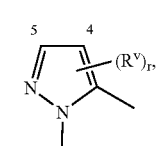
U-11

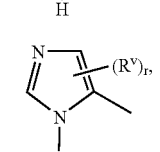
U-12

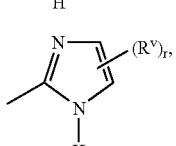
U-13

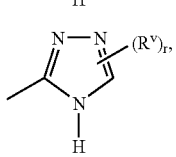
U-14

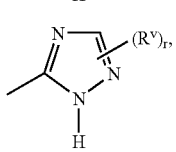
U-15

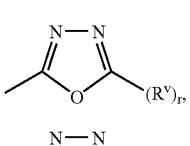
U-16

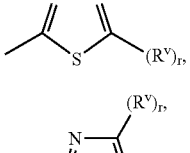
U-17

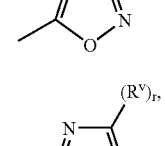
U-18

U-19

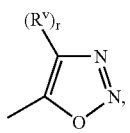 U-20
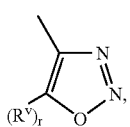 U-21
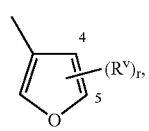 U-22
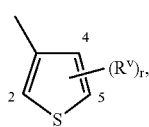 U-23
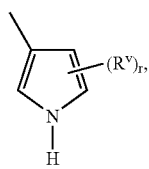 U-24
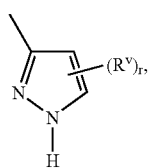 U-25
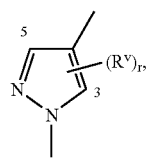 U-26
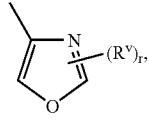 U-27
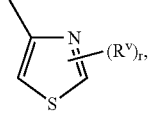 U-28
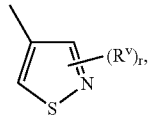 U-29
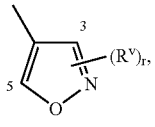 U-30
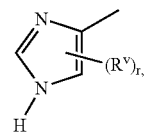 U-31
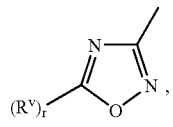 U-32
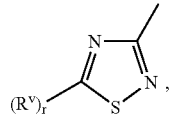 U-33
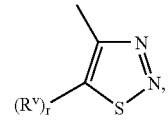 U-34
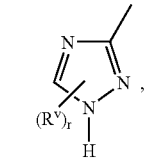 U-35
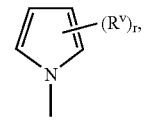 U-36
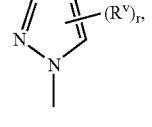 U-37
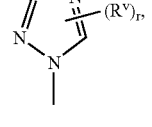 U-38
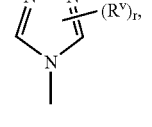 U-39
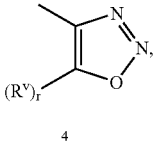 U-40
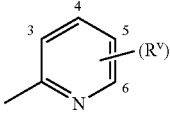 U-41
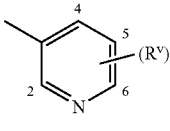 U-42

-continued
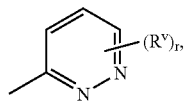 U-43
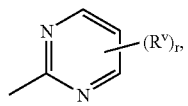 U-44
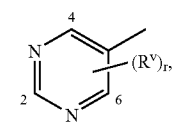 U-45
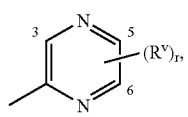 U-46
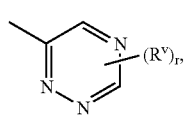 U-47
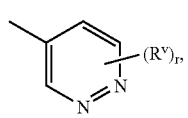 U-48
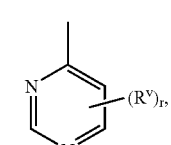 U-49
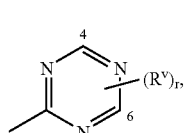 U-50
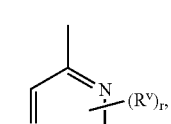 U-51
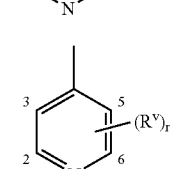 U-52
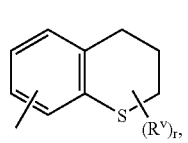 U-53
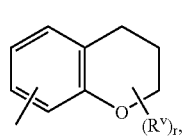 U-54
-continued
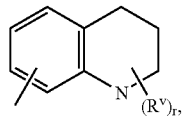 U-55
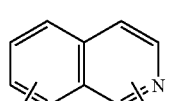 U-57
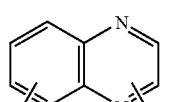 U-58
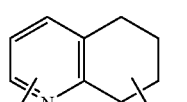 U-59
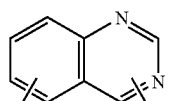 U-60
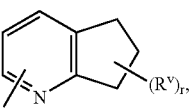 U-61
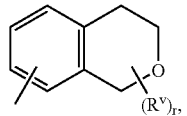 U-62
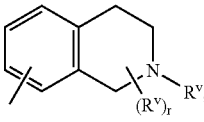 U-63
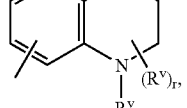 U-64
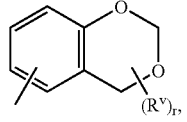 U-65
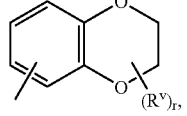 U-66
U-67

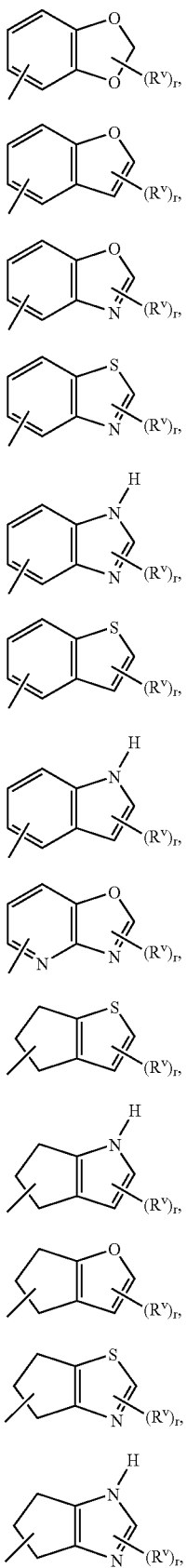
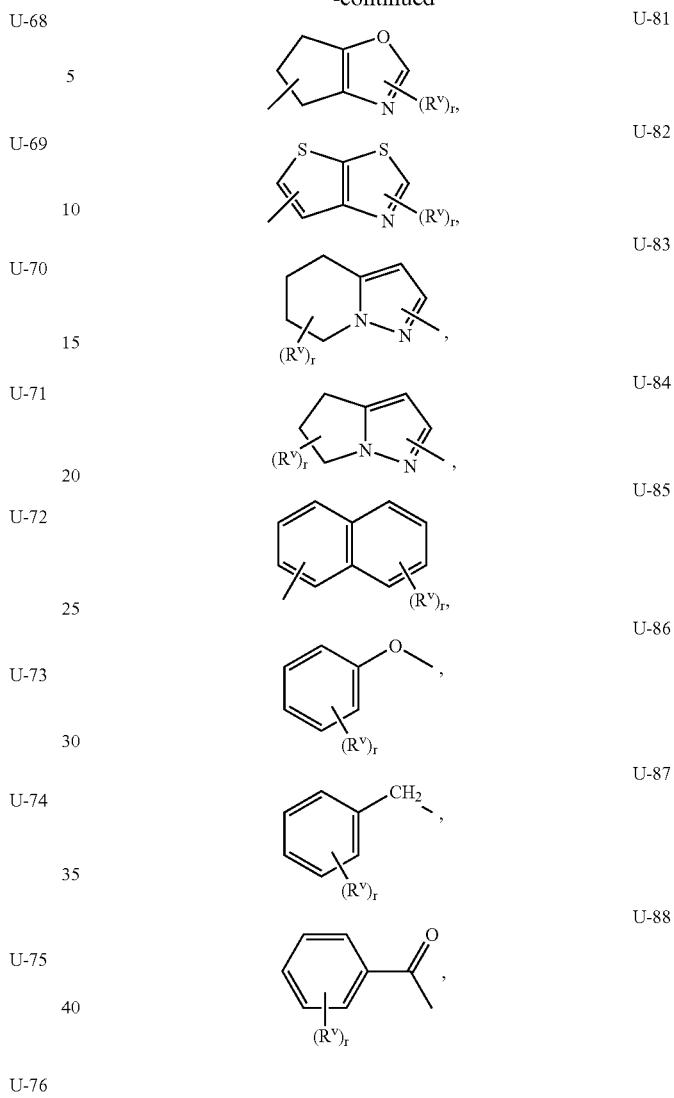

As noted above, K is taken together with the two contiguous linking atoms to form a 5- or 6-membered nonaromatic carbocyclic or heterocyclic ring optionally including one or two ring members selected from the group consisting of C(=O), SO and S(O)$_2$, each ring optionally substituted with 1 to 4 R$^4$. The dashed line in Formula I means that the indicated bond may be optionally a single bond or a double bond. Other bonds comprising K may also be single bonds or double bonds. The term "optionally substituted" in connection with these K rings refers to rings which are (other than the amide substituents indicated in Formula I) unsubstituted or have at least one non-hydrogen substituent that does not extinguish the biological activity possessed by the unsubstituted analog. Examples of 5- or 6-membered non-aromatic carbocyclic or heterocyclic rings optionally substituted with 1 to 4 R$^4$ include the rings K-1 through K-53 illustrated in Exhibit 2. In these examples the wavy lines indicate the amide moieties are attached to K as shown, wherein the upper right bond is attached to the NR$^1$C(=A)J moiety and the lower right bond is attached to the C(=B)NR$^2$R$^3$ moiety. R$^{13}$ is H or a subset of R$^4$ and is selected from H, C$_1$–C$_4$ alkyl or C$_1$–C$_4$ haloalkyl.

Exhibit 2
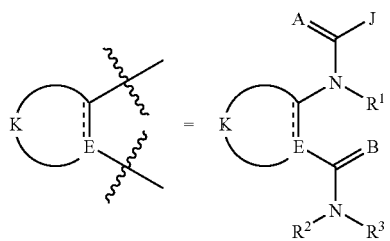
I
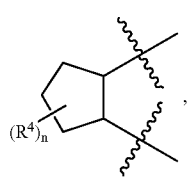
K-1
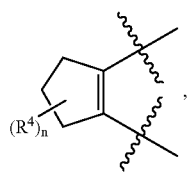
K-2
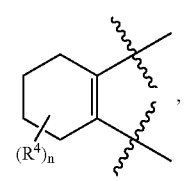
K-3
K-4
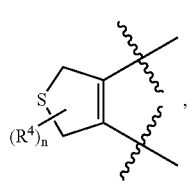
K-5
K-6
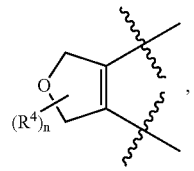
K-7
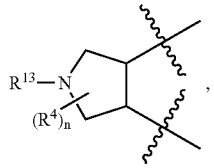
K-8
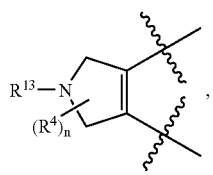
K-9
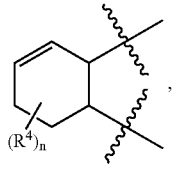
K-10
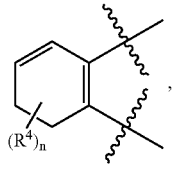
K-11
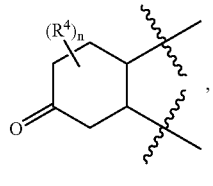
K-12
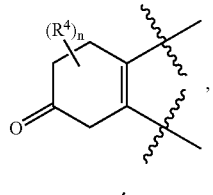
K-13
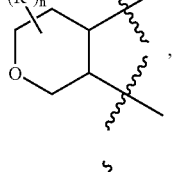
K-14
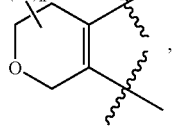
K-15
K-16

-continued
K-17
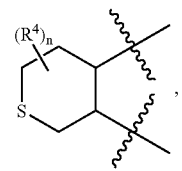
K-18
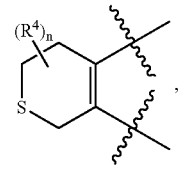
K-19
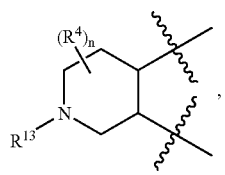
K-20
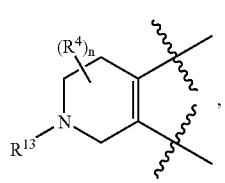
K-21
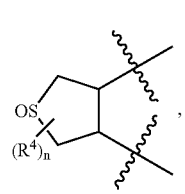
K-22
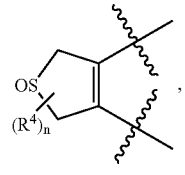
K-23
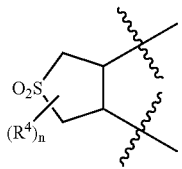
K-24
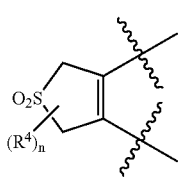
K-25
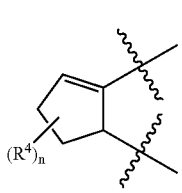
-continued
K-26
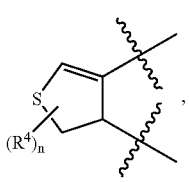
K-27
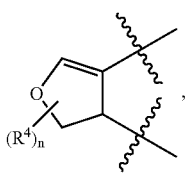
K-28
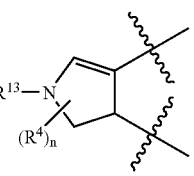
K-29
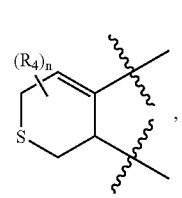
K-30
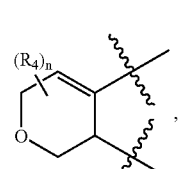
K-31
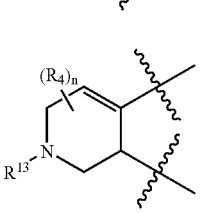
K-32
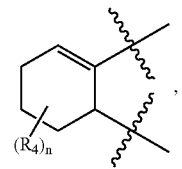
K-33
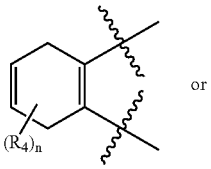 or -continued

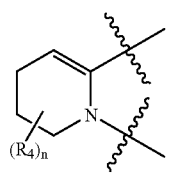
K-34

As noted above, R³ can be (among others) $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of a phenyl ring and 5- or 6-membered heteroaromatic ring, each ring optionally substituted with one to three substituents independently selected from $R^6$. Examples of such rings incorporated into said R³ groups include the rings illustrated as U-1 through U-53 and U-86 illustrated in Exhibit 1, except that such rings are optionally substituted with 1 to 3 substituents independently selected from $R^6$ rather than $(R^v)_r$ and are attached to an R³ group selected from the list immediately above.

As noted above, R³ can be (among others) G; or $C_1$–$C_6$ alkyl, $C_2$–$C_6$ alkenyl $C_2$–$C_6$ alkynyl, $C_3$–$C_6$ cycloalkyl, each optionally substituted with G; wherein G is a 5- or 6-membered nonaromatic carbocyclic or heterocyclic ring, optionally including one or two ring members selected from the group consisting of C(=O), SO and S(O)$_2$ and optionally substituted with 1 to 4 substituents selected from $R^{12}$. The term "optionally substituted" in connection with these G groups refers to groups which are unsubstituted or have at least one non-hydrogen substituent that does not extinguish the biological activity possessed by the unsubstituted analog. The optional substituents can be attached to any available carbon by replacing a hydrogen atom. Examples of 5- or 6-membered nonaromatic carbocyclic rings as G include the rings illustrated as G-1 through G-8 of Exhibit 3. Examples of 5- or 6-membered nonaromatic heterocyclic rings as G include the rings illustrated as G-9 through G-38 of Exhibit 3. Note that when G comprises a ring selected from G-31 through G-34, G-37 and G-38, $Q^1$ is selected from O, S or N. Note that when G is G-11, G13, G-14, G16, G-23, G-24, G-30 through G-34, G-37 and G-38 and $Q^1$ is N, the nitrogen atom can complete its valence by substitution with either H or $C_1$–$C_2$ alkyl. Note that when the attachment point on the G group is illustrated as floating, the G group can be attached to the remainder of Formula I through any available carbon of the G group by replacement of a hydrogen atom.

Exhibit 3

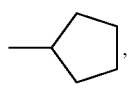
G-1

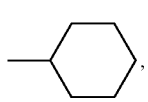
G-2

G-3

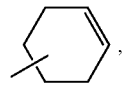
G-4

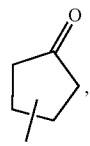
G-5

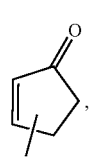
G-6

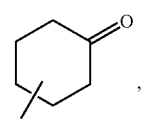
G-7

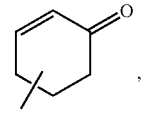
G-8

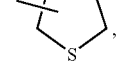
G-9

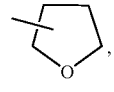
G-10

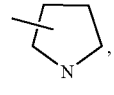
G-11

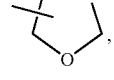
G-12

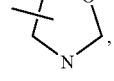
G-13

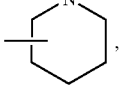
G-14

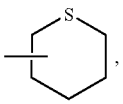
G-15

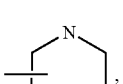
G-16

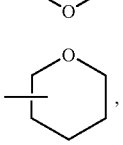
G-17

-continued

G-18 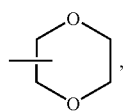

G-19 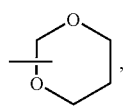

G-20 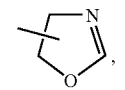

G-21 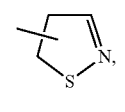

G-22 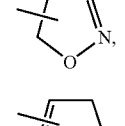

G-23 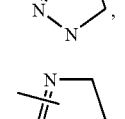

G-24 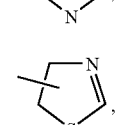

G-25 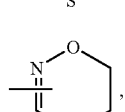

G-26 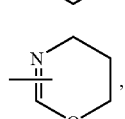

G-27 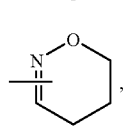

G-28 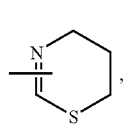

G-29 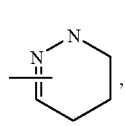

G-30 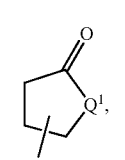

G-31 

-continued

G-32 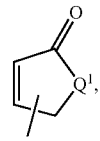

G-33 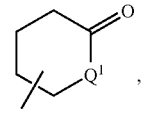

G-34 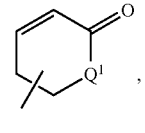

G-35, G-36 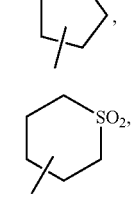

G-37 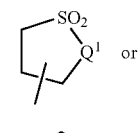

G-38 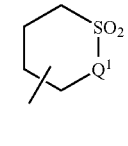

As noted above, each $R^4$ can be independently (among others) a phenyl, benzyl, phenoxy or 5- or 6-membered heteroaromatic ring, each ring optionally substituted with one to three substituents independently selected from $R^6$. Examples of such $R^4$ groups include the rings or ring systems illustrated as U-1 through U-53, U-86 and U-87 illustrated in Exhibit 1, except that such rings are optionally substituted with 1 to 3 substituents independently selected from $R^6$ rather than $(R^v)_r$.

As noted above, each $R^5$ can be independently (among others) a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from $R^6$. Examples of such $R^5$ groups include the rings or ring systems illustrated as U-1 through U-88 illustrated in Exhibit 1, except that such rings are optionally substituted with 1 to 3 substituents independently selected from $R^6$ rather than $(R^v)_r$.

Preferred compounds for reasons of better activity and/or ease of synthesis are:

Preferred 1. Compounds of Formula I above, their N-oxides and agriculturally suitable salts thereof, wherein A and B are both O and J is a phenyl group optionally substituted with 1 to 4 $R^5$.

Preferred 2. Compounds of Preferred 1 wherein
each $R^4$ is independently $C_1$–$C_4$ alkyl, $C_1$–$C_4$ haloalkyl, halogen, CN, $NO_2$ or $C_1$–$C_4$ alkoxy, and one $R^4$ group is attached to the K ring at the carbon adjacent to either the NR$^1$C(=A)J moiety or the C(=B)NR$^2$R$^3$ moiety; and each R$^5$ is independently halogen, C$_1$–C$_4$ alkyl C$_1$–C$_4$ alkoxy, C$_1$–C$_4$ haloalkyl, CN, NO$_2$, C$_1$–C$_4$ haloalkoxy, C$_1$–C$_4$ alkylthio, C$_1$–C$_4$ alkylsulfinyl, C$_1$–C$_4$ alkylsulfonyl, C$_1$–C$_4$ haloalkylthio, C$_1$–C$_4$ haloalkylsulfinyl, C$_1$–C$_4$ haloalkylsulfonyl or C$_2$–C$_4$ alkoxycarbonyl; or each R$^5$ is independently a phenyl or a 5- or 6-membered heteroaromatic ring, each ring optionally substituted with one to three substituents independently selected from R$^6$; or two R$^5$ groups when attached to adjacent carbon atoms can be taken together as —OCF$_2$O—, —CF$_2$CF$_2$O— or —OCF$_2$CF$_2$O—.

Preferred 3. Compounds of Preferred 2 wherein

R$^1$ and R$^2$ are both H;

R$^3$ is C$_1$–C$_4$ alkyl optionally substituted with 1 to 5 substituents independently selected from the group consisting of halogen, CN, OCH$_3$ and S(O)$_p$CH$_3$;

each R$^4$ is independently CH$_3$, CF$_3$, CN or halogen, and one R$^4$ group is attached to the K ring at the carbon adjacent to the NR$^1$C(=A)J moiety;

each R$^5$ is independently halogen, methyl, CF$_3$, OCF$_3$, OCHF$_2$, S(O)$_p$CF$_3$, S(O)$_p$CHF$_2$, OCH$_2$CF$_3$, OCF$_2$CHF$_2$, S(O)$_p$CH$_2$CF$_3$ or S(O)$_p$CF$_2$CHF$_2$; or a phenyl, pyrazole, imidazole, triazole, pyridine or pyrimidine ring, each ring optionally substituted with one to three substituents independently selected from the group consisting C$_1$–C$_4$ alkyl, C$_1$–C$_4$ haloalkyl, halogen and CN; and p is 0, 1 or 2.

Preferred 4. Compounds of Preferred 3 wherein R$^3$ is C$_1$–C$_4$ alkyl.

Preferred 5. Compounds of Formula I above, their N-oxides and agriculturally suitable salts thereof wherein A and B are both O;

J is a 5- or 6-membered heteroaromatic ring selected from the group consisting of J-1, J-2, J-3, J-4 and J-5, each J optionally substituted with 1 to 3 R$^5$

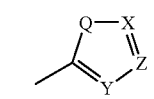
J-1

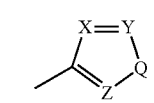
J-2

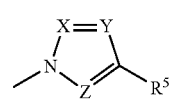
J-3

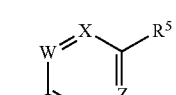
J-4

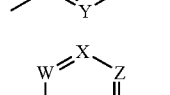
J-5

Q is O, S, NH or NR$^5$; and

W, X, Y and Z are independently N, CH or CR$^5$, provided that in J4 and J-5 at least one of W, X, Y or Z is N.

Preferred 6. Compounds of Preferred 5 wherein each R$^4$ is independently C$_1$–C$_4$ alkyl C$_1$–C$_4$ haloalkyl, halogen, CN, NO$_2$ or C$_1$–C$_4$ alkoxy, and one R$^4$ group is attached to the K ring at the carbon adjacent to either the NR$^1$C(=A)J moiety or the C(=B)NR$^2$R$^3$ moiety; and each R$^5$ is independently C$_1$–C$_4$ alkyl, C$_1$–C$_4$ haloalkyl, halogen, CN, NO$_2$, C$_1$–C$_4$ haloalkoxy, C$_1$–C$_4$ alkylthio, C$_1$–C$_4$ alkylsulfinyl, C$_1$–C$_4$ alkylsulfonyl, C$_1$–C$_4$ haloalkylthio, C$_1$–C$_4$ haloalkylsulfinyl, C$_1$–C$_4$ haloalkylsulfonyl or C$_2$–C$_4$ alkoxycarbonyl;

each R$^5$ is independently a phenyl or a 5- or 6-membered heteroaromatic ring, each ring optionally substituted with one to three substituents independently selected from R$^6$.

Preferred 7. Compounds of Preferred 6 wherein

J is selected from the group consisting of

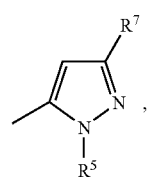
J-6

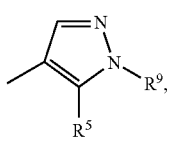
J-7

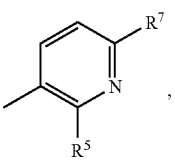
J-8

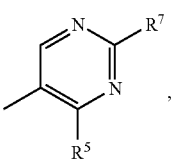
J-9

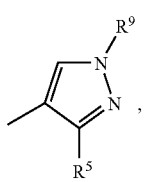
J-10

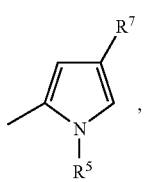
J-11

-continued

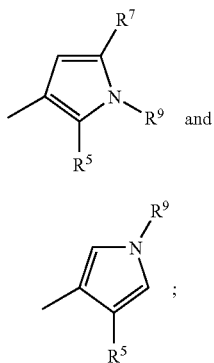

J-12

J-13

$R^5$ is $C_1$–$C_4$ alkyl, $C_1$–$C_4$ haloalkyl, or

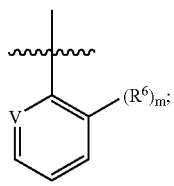

V is N, CH, CF, CCl, CBr or CI;
$R^6$ is $C_1$–$C_6$ alkyl, $C_3$–$C_6$ cycloalkyl, $C_1$–$C_4$ haloalkyl, halogen, CN, $C_1$–$C_4$ alkoxy, $C_1$–$C_4$ haloalkoxy or $C_1$–$C_4$ haloalkylthio;
each $R^7$ is independently H, $C_1$–$C_6$ alkyl, $C_3$–$C_6$ cycloalkyl, $C_1$–$C_4$ haloalkyl, halogen, CN, $C_1$–$C_4$ alkoxy, $C_1$–$C_4$ haloalkoxy or $C_1$–$C_4$ haloalkylthio;
each $R^9$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl; provided $R^7$ and $R^9$ are not both H; and
m is 0 or 1.

Preferred 8. Compounds of Preferred 7 wherein V is N.
Preferred 9. Compounds of Preferred 7 wherein V is CH, CF, CCl or CBr.
Preferred 10. Compounds of Preferred 8 or Preferred 9 wherein
$R^1$ and $R^2$ are both H;
$R^3$ is $C_1$–$C_4$ alkyl optionally substituted with 1 to 5 substituents independently selected from the group consisting of halogen, CN, $OCH_3$ and $S(O)_pCH_3$;
each $R^4$ is independently $CH_3$, $CF_3$, CN or halogen, and one $R^4$ group is attached to the K ring at the carbon adjacent to the $NR^1C(=A)J$ moiety;
$R^6$ is $C_1$–$C_4$ alkyl, $C_1$–$C_4$ haloalkyl, halogen or CN;
$R^7$ is H, $CH_3$, $CF_3$, $OCHF_2$ or halogen;
p is 0, 1 or 2; and
m is 1.

Preferred 11. Compounds of Preferred 10 wherein $R^3$ is $C_1$–$C_4$ alkyl; each $R^4$ group is independently $CH_3$, Cl, Br or I; and an optionally second $R^4$ is F, Cl, Br, I, CN or $CF_3$.
Preferred 12. Compounds of Preferred 11 wherein J is J-6; $R^6$ is halogen; and $R^7$ is halogen or $CF_3$.
Preferred 13. Compounds of Preferred 12 wherein V is N; $R^3$ is methyl, ethyl, isopropyl or tertiary butyl and $R^7$ is Br, Cl or $CF_3$.

Preferred 14. Compounds of Preferred 11 wherein J is J-7; $R^6$ is halogen; and $R^9$ is $CF_3$, $CHF_2$, $CH_2CF_3$ or $CF_2CHF_2$.
Preferred 15. Compounds of Preferred 11 wherein J is J-8; $R^6$ is halogen; and $R^7$ is halogen or $CF_3$.
Preferred 16. Compounds of Preferred 11 wherein J is J-9; $R^6$ is halogen; and $R^7$ is $CF_3$.
Preferred 17. Compounds of Preferred 11 wherein J is J-10; $R^6$ is halogen; and $R^9$ is $CF_3$, $CHF_2$, $CH_2CF_3$ or $CF_2CHF_2$.
Preferred 18. Compounds of Preferred 11 wherein J is J-11; $R^6$ is halogen; and $R^7$ is halogen or $CF_3$.
Preferred 19. Compounds of Preferred 11 wherein J is J-12; $R^6$ is halogen; $R^7$ is H, halogen or $CF_3$, and $R^9$ is H, $CF_3$, $CHF_2$, $CH_2CF_3$, or $CF_2CHF_2$.
Preferred 20. Compounds of Preferred 11 wherein J is J-13; $R^6$ is halogen; $R^7$ is H, halogen or $CF_3$, and $R^9$ is H, $CF_3$, $CHF_2$, $CH_2CF_3$ or $CF_2CHF_2$.

Most preferred are compounds of Preferred 12 selected from the group:
3-Bromo-1-(3-chloro-2-pyridinyl)-N-[2-methyl-6-[[(1-methylethyl)amino]carbonyl]-1-cyclohexen-1-yl]-1H-pyrazole-5-carboxamide and
1-(3-Chloro-2-pyridinyl)-N-[4,5-dihydro-2-methyl-4-[[[(1-methylethyl)amino]carbonyl]-3-thienyl]-3-(trifluoromethyl)-1H-pyrazole-5-carboxamide.

This invention also pertains to a composition for controlling an invertebrate pest comprising a biologically effective amount of a compound of Formula I, an N-oxide thereof or a suitable salt thereof and at least one additional component selected from the group consisting of surfactants, solid diluents and liquid diluents. This invention also pertains to a composition comprising a biologically effective amount of a compound of Formula I, an N-oxide thereof or a suitable salt thereof and an effective amount of at least one additional biologically active compound or agent. The preferred compositions of the present invention are those which comprise the above preferred compounds.

This invention also pertains to a method for controlling an invertebrate pest comprising contacting the invertebrate pest or its environment with a biologically effective amount of a compound of Formula I, an N-oxide thereof or a suitable salt thereof (e.g., as a composition described herein). This invention also relates to such a method wherein the invertebrate pest or its environment is contacted with a biologically effective amount of a compound of Formula I or a composition comprising a compound of Formula I, an N-oxide thereof or a suitable salt thereof and a biologically effective amount of at least one additional compound or agent for controlling invertebrate pests. The preferred methods of use are those involving the above preferred compounds.

Compounds of Formula I can be prepared by one or more of the following methods and variations as described in Schemes 1–17. The definitions of A, B, J, K, $R^1$, $R^2$ and $R^3$ in compounds of Formulae 2–13 are as defined above in the Summary of Invention. Compounds of Formula Ia–c, 2a–d, 3a–c and 7a–c are various subsets of Formulae I, 2, 3 and 7, respectively.

A typical procedure for preparing compounds of Formula I is detailed in Scheme 1 and involves amidation of an ester of Formula 2 with an amine optionally in the presence of a Lewis Acid, e.g. trimethylaluminum. R' in all schemes below is a lower alkyl or phenyl or pyridyl group.

Scheme 1

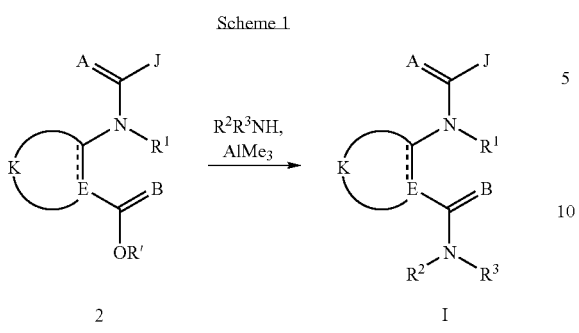

Compounds of Formula 2 can be prepared by the method detailed in Scheme 2 and involves coupling of an amine of Formula 3 with an acid chloride of Formula 4 in the presence of an acid scavenger to provide a compound of Formula 2a. Methods for the preparation of typical compounds of Formula 4 are detailed in WO01/070671. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. In a subsequent step, amides of Formula 2a can be converted to thioamides of Formula 2b using a variety of standard thio transfer reagents including phosphorus pentasulfide and (2,4-bis(4-methoxyphenyl)-1,3-dithia-2,4-diphosphetane-2,4-disulfide).

Scheme 2

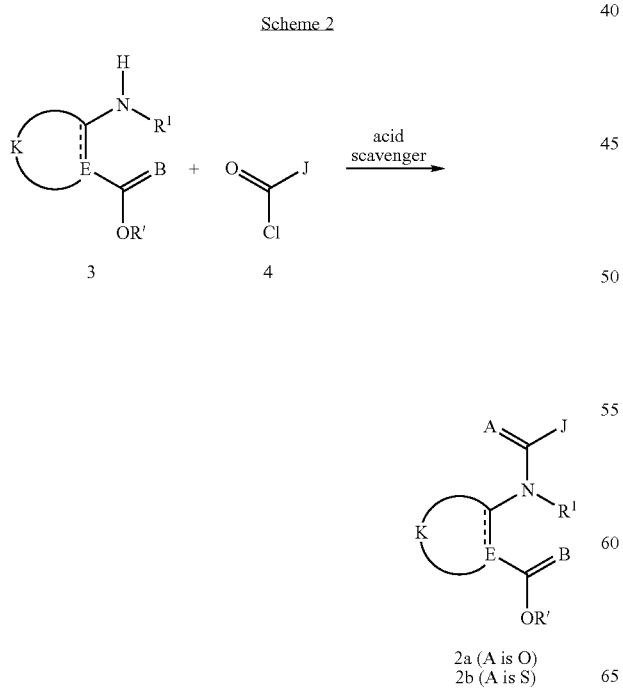

As illustrated in Scheme 3, an alternate method for the preparation of compounds of Formula 2a involves coupling of an amine of Formula 3 with an acid of Formula 5 in the presence of a dehydrating agent such as dicyclohexylcarbodiimide (DCC). Polymer supported reagents are again useful here, such as polymer-bound cyclohexylcarbodiimide. The synthetic methods of Schemes 2 and 3 are just representative examples of a wide variety of coupling methods useful for the preparation of Formula 2 compounds; the synthetic literature is extensive for this type of coupling reaction.

Scheme 3

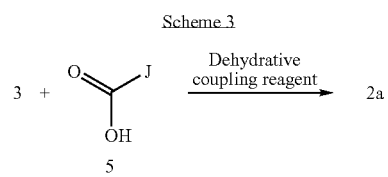

One skilled in the art will also realize that the acid chlorides of Formula 4 can be prepared from acids of Formula 5 by numerous well-known methods. For example, acid chlorides of Formula 4 are readily made from carboxylic acids of Formula 5 by reacting the carboxylic acid 5 with thionyl chloride or oxalyl chloride in an inert solvent such as toluene or dichloromethane in the presence of a catalytic amount of N,N-dimethylformamide.

Amines of Formula 3a can be prepared through the reaction of compounds of Formula 6 with zinc metal as shown in Scheme 4.

Scheme 4

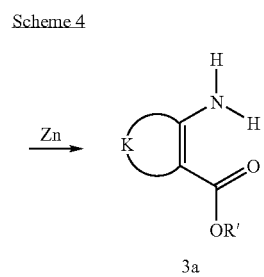

As illustrated in Scheme 5, compounds of Formula 2d or 3c can be obtained from compounds of Formula 2c or enamines of Formula 3b respectively by treatment with hydrogen at pressures from 1 to 100 atmospheres, or with a hydrogen source such as cyclohexene, in the presence of a suitable transition metal catalyst such as palladium supported on carbon or platinum oxide (*J. Org. Chem.*, 1968, 33(3), 1287).

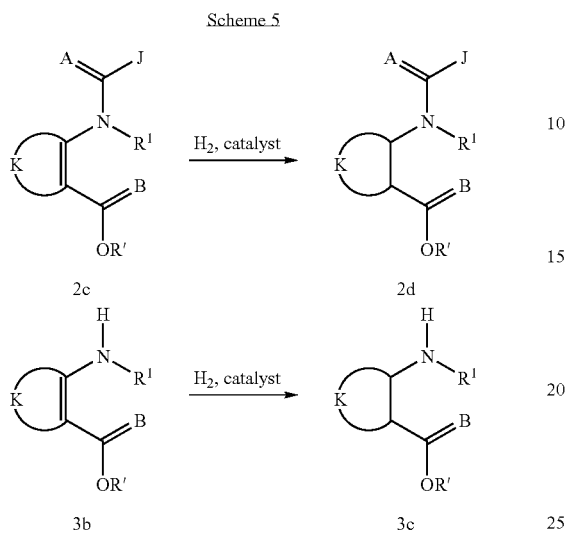

Scheme 5

As illustrated in Scheme 6, amines of Formula 3 are typically available from the corresponding β-ketoesters of Formula 7 via amination of the keto group. Typical procedures involve treatment with ammonia or its salts such as ammonium acetate to give compounds of Formula 3a. The reaction is carried out in suitable solvents such as ethanol, dioxane or hexane with or without acid catalysts such as ammonium nitrate or p-toluene sulfonic acid. Compounds of Formula 3a can also be prepared from compounds of Formula 7 by reaction with trimethylsilyliminotriphenyl phosphorane as described in *J. Org. Chem.*, 1978, 43(7), 1460. Compounds of Formula 3b, wherein $R^1$ is alkyl or substituted alkyl, can also be prepared using these methods by replacing the ammonia with a primary amine or a suitable salt thereof.

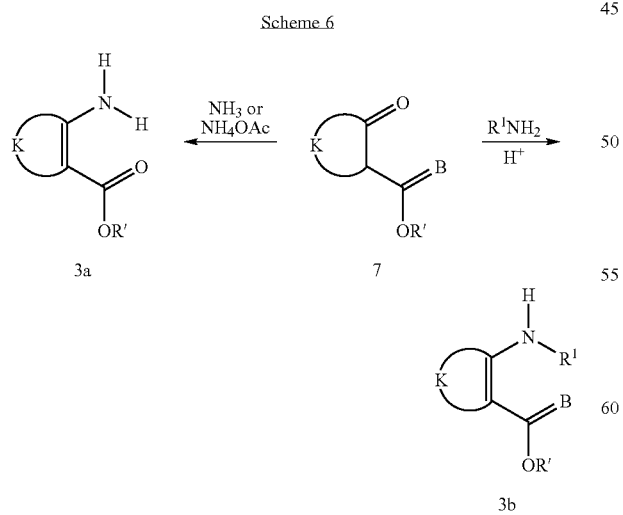

Scheme 6

($R^1$ is other than H)

Schemes 7 through 12 illustrate various methods to prepare compounds of Formula 7 and their subsets of Formula 7b, 7c and 7d.

As illustrated in Scheme 7, $R^4$ substituents can be introduced alpha to the keto group of the β-ketoesters of Formula 7a by alkylation to give compounds of Formula 7b according to *J. Am. Chem. Soc.*, 1974, 96(4), 1082.

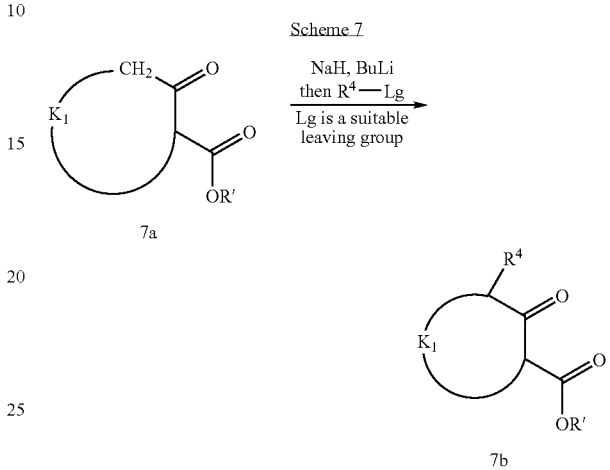

Scheme 7

$K_1$ is a 2- or 3-atom linking chain

As illustrated in Scheme 8, β-ketoesters of Formula 7c can be prepared by Dieckman cyclization of a bis-ester of Formula 8 according to procedures well known in the art.

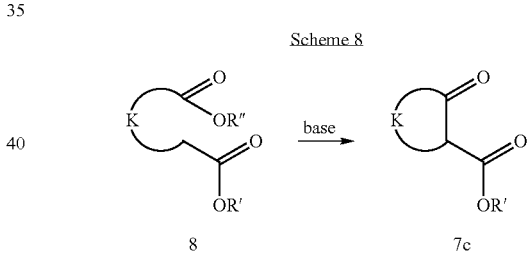

Scheme 8

As illustrated in Scheme 9, β-ketoesters of Formula 7 can be prepared by Claisen condensation of cyclic ketones of Formula 9 with carboxyl or thiocarboxyl donors, such as ethyl carbonate or di-tolylthiocarbonate, in the presence of a suitable base such as sodium hydride or lithium diisopropylamide. Lg is a nucleophilic displaceable leaving group such as halide, alkyl or aryl sulfonates and alkyl sulfates.

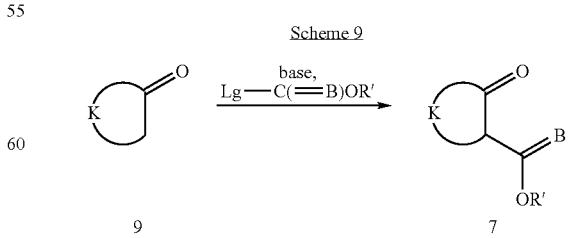

Scheme 9

As illustrated in Scheme 10, β-ketoesters of Formula 7c can be prepared by the reaction of a cyclic ketone of Formula 9 with a diazoacetate such as ethyl diazoacetate in the presence of a Lewis Acid or triethyloxonium tetrafluoroborate (Scheme 10).

Scheme 10

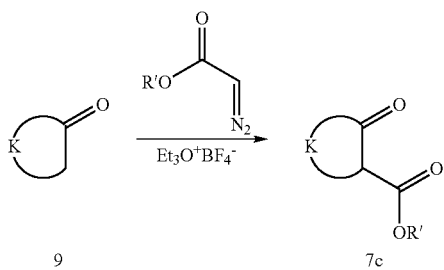

As illustrated in Scheme 11, β-ketoesters of Formula 7 can also be prepared by acylation of a cyclic enamine of Formula 10 followed by hydrolysis (*J. Am. Chem. Soc.*, 1963, 85, 207). Lg is as defined above for Scheme 9.

Scheme 11

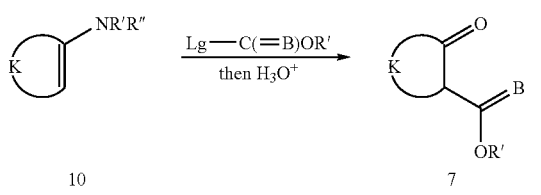

As illustrated in Scheme 12, β-ketoesters of Formula 7d can be prepared by intramolecular alkylation or acylation of an acyclic β-ketoester of Formula 11, wherein Lg is as defined above for Scheme 9, in the presence of a suitable base such as potassium carbonate.

Scheme 12

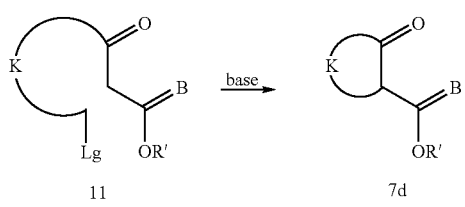

Alternatively, compounds of Formula Ia can be prepared according to the methods of Schemes 2 and 3 from compounds of Formula 12 as shown in Scheme 13. In a subsequent step, amides of Formula Ia can be converted to thioamides of Formula Ib using a variety of standard thio transfer reagents including phosphorus pentasulfide and Lawesson's Reagent.

Scheme 13

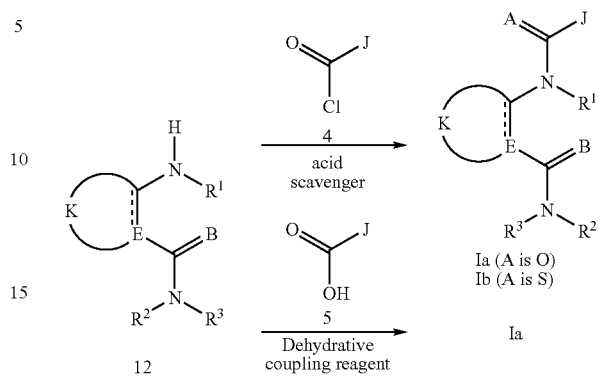

As shown in Scheme 14, compounds of Formula 12 and 12a can be prepared according to the method of Scheme 6 from compounds of Formula 13.

Scheme 14

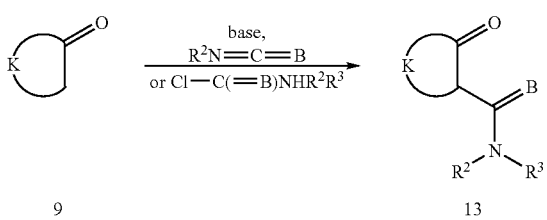

Compounds of Formula 13 can be prepared according to the method of Scheme 15 from compounds of Formula 9 through the action of a base and an isocyanate of Formula 14 or a carbamoyl chloride of Formula 15.

Scheme 15

Compounds of Formula Ic wherein K is K-34 can be prepared by the procedures outlined in Schemes 16–17. Acylation of compounds of Formula 14 with, for example, an alkyl isocyanate or a carbamoyl chloride, followed by treatment with a suitable reducing agent, for example sodium borohydride, can furnish compounds of Formula Ic.

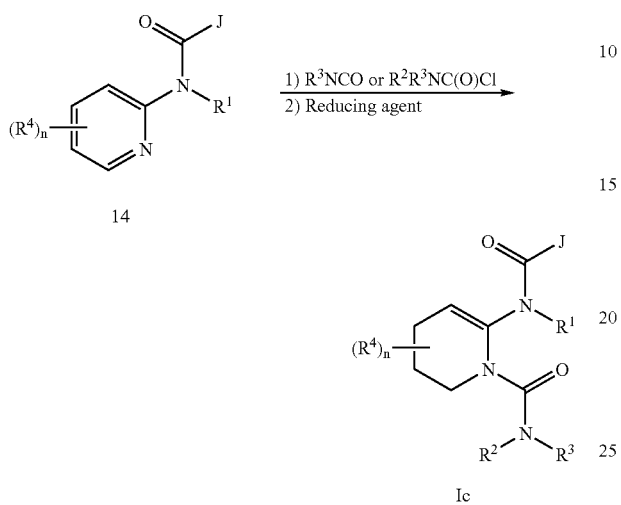

Compounds of Formula 14 can be prepared by the coupling of an aminopyridine of Formula 16 with an acid chloride of Formula 4 or an acid of Formula 5 according to the methods described in Schemes 2 and 3 respectively.

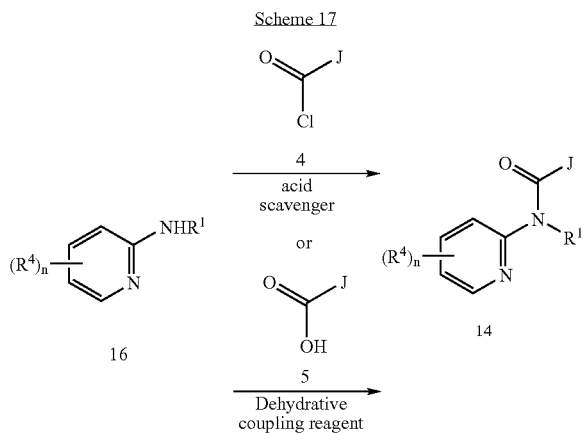

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

1-(3-Chloro-2-pyridinyl)-N-[4,5-dihydro-2-methyl-4-[[(1-methylethyl)amino]carbonyl]-3-thienyl]-3-(trifluoromethyl)-1H-pyrazole-5-carboxamide Step A: Preparation of Ethyl 2-[(3-methoxy-3-oxopropyl)thio]propanoate To a mixture of methyl acrylate (9.5 g, 110 mmol) and ethyl 2-thiopropionate (14.8 g, 99 mmol) was added piperidine (0.1 mL, 1.0 mmol). The resulting exotherm was controlled with an ice bath and the mixture was stirred overnight at ambient temperature to give the crude title product.

$^1$H NMR (CDCl$_3$) δ 4.2 (q, 2H), 3.70 (s, 3H), 3.42 (q, 1H), 3.0–2.8 (m, 2), 1.44 (d, 3H), 1.30 (t, 3H).

Step B: Preparation of Ethyl 4-amino-2,5-dihydro-5-methyl-3-thiophenecarboxylate A solution of the product of Step A (17.24 g, 73 mmol) in toluene (160 mL) was treated with potassium t-butoxide (18.4 g, 164 mmol) and the mixture was heated at reflux for 1.5 h. Upon cooling to ambient temperature, the mixture was washed twice with 1 N hydrochloric acid, dried over magnesium sulfate and concentrated. To a solution of the resulting residue (11.0 g) in ethanol (150 mL) was added ammonium formate (32.3 g, 0.51 mol) and the mixture was heated at reflux for 7 h and then stirred at ambient temperature overnight. The mixture was diluted with ethyl ether, washed with water (2×) and dried over magnesium sulfate to give the title product as a yellow oil, 7.05 g. The material was a mixture of methyl and ethyl esters.

Data for ethyl ester: $^1$H NMR (CDCl$_3$) δ 6.2–5.5 (bs, 2H), 4.21–4.14 (m, 3H), 3.9–3.7 (AB m,2H), 1.51 (d, 3H), 1.28 (t, 3H).

Step C: Preparation of 3-Chloro-2-[3-(trifluoromethyl)-1H-pyrazol-1-yl]pyridine

To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110–125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139–141° C., 7 mm) afforded the title product as a clear yellow oil (113.4 g). $^1$H NMR (CDCl$_3$) δ 6.78 (s, 1H), 7.36 (t, 1H), 7.93 (d, 1H), 8.15 (s, 1H), 8.45 (d, 1H).

Step D: Preparation of 1-(3-Chloro-2-pyridinyl)-3-(trifluoromethyl)-1H-pyrazole-5-carboxylic acid To a solution of 3-chloro-2-[3-(trifluoromethyl)-1H-pyrazol-1-yl]pyridine (i.e. the product of Step C) (105.0 g, 425 mmol) in dry tetrahydrofuran (700 mL) at −75° C. was added via cannula a −30° C. solution of lithium diisopropylamide (425 mmol) in dry tetrahydrofuran (300 mL) to afford a deep red solution. After stirring for 15 minutes, carbon dioxide was bubbled through at −63° C. until the solution became pale yellow and the exothermicity ceased. The reaction mixture was stirred for an additional 20 minutes and then quenched with water (20 mL). The solvent was removed under reduced pressure, and the reaction mixture was partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5–3. The orange oil congealed into a granular solid, which was filtered, washed successively with water and 1N hydrochloric acid, and dried under vacuum at 50° C. to afford the title product as an off-white solid (130 g). (Product from another run following similar procedure melted at 175–176° C.)

$^1$H NMR (DMSO-d$_6$) δ 7.61 (s, 1H), 7.76 (dd, 1H), 8.31 (d, 1H) 8.60 (d, 1H).

Step E: Preparation of Ethyl 4-[[[1-(3-chloro-2-pyridinyl)-3-(trifluoromethyl)-1H-pyrazol-5-yl]carbonyl]amino]-2,3-dihydro-5-methyl-3-thiophenecarboxylate To a suspension of 1-(3-chloro-2-pyridinyl)-3-(trifluoromethyl)-1H-pyrazole-5-carboxylic acid (i.e. the product of Step D (1.11 g, 3.81 mmol) in dichloromethane (10 mL) was added dimethylformamide (20 μL) and oxalyl chloride (450 μL, 5.16 mmol) and the mixture was stirred at ambient temperature for 3 hrs. The resulting solution was concentrated under reduced pressure and placed under high vacuum (0.1 torr) for 0.5 hour. The residue was re-dissolved in acetone (5 mL) and added to a mixture of the title compound of Step B (0.665 g, 3.8 mmol) and potassium carbonate (0.787 g, 5.7 mmol) in acetone (10 mL) and the mixture was stirred overnight at ambient temperature. The reaction was quenched with a saturated solution of sodium bicarbonate and the mixture was filtered through a column of celite, washing with dichloromethane. The eluent was concentrated and purified by silica gel column chromatography (20% then 40% then 60% then 80% ethyl ether in petroleum ether) to give the title compound mixed with its methyl ester as a yellow solid (0.8 g).

Data for ethyl ester: $^1$H NMR (CDCl$_3$) δ 8.50 (dd, 1H), 7.93 (dd, 1H), 7.71 (bs, 1H), 7.46 (dd, 1H), 7.05 (s, 1H), 4.20 (q, 2H), 4.10 (q, 1H), 3.5–3.4 (m, 2H, 1.83 (s, 3H), 1.28 (t, 3H).

Step F: Preparation of 1-(3-Chloro-2-pyridinyl)-N-[4,5-dihydro-2-methyl-4-[[(1-methylethyl)amino]carbonyl]-3-thienyl]-3-(trifluoromethyl)-1H-pyrazole-5-carboxamide Isopropyl amine (170 μL, 1.9 mmol) was added to a solution of trimethylaluminum (1 mL, 2 M solution in hexanes, 1.9 mmol) in dichloromethane (10 mL) and the solution was stirred at ambient temperature for 0.75 hour. The product of Step E was then added (425 mg, 0.9 mmol) and the solution was heated at reflux overnight. The reaction was quenched with water and the organic layer was separated and dried over magnesium sulfate. Concentration and purification by silica gel column chromatography (60% then 80% ethyl ether in petroleum ether) gave the title compound, a compound of present invention, as a yellow solid (151 mg).

$^1$H NMR (CDCl$_3$) δ 8.81 (bs, 1H), 8.48 (dd, 1H), 7.93 (dd, 1H), 7.47 (dd, 1H), 6.16 (bd, 1H), 4.03–3.84 (m, 2H), 3.40 (m, 1H), 3.38 (m, 1H), 1.87 (d, 3H), 0.99 (d, 3H), 0.95 (d, 3H).

EXAMPLE 2

3-Bromo-1-(3-chloro-2-pyridinyl-N-[6-methyl-2-[[(1-methylethyl)amino]carbonyl]-1-cyclohexen-1-yl]-1H-pyrazole-5-carboxamide Step A: Preparation of Ethyl 3-methyl-2-oxocyclohexanecarboxylate To a suspension of sodium hydride (5.0 g, 0.125 mol) in tetrahydrofuran (250 mL) was added a solution of ethyl 2-oxocyclohexanecarboxylate (19.9 mL, 0.125 mol) in tetrahydrofuran (30 mL) whilst maintaining the temperature of the mixture between 10° C. and 15° C. by means of an ice bath. After stirring at 5° C. for 1 hour, butyl lithium (52.5 mL, 2.5 M solution in hexanes, 131 mmol) was added dropwise while maintaining the temperature below 12° C. After stirring at 5° C. for 30 minutes, iodomethane (7.8 mL, 125 mmol) was added. The reaction mixture was stirred at 5° C. for 1.5 hours and then quenched with a saturated solution of ammonium chloride. The mixture was diluted with ethyl ether, washed with water. The organic extracts were dried over magnesium sulfate and concentrated. The resulting residue was distilled (100–110° C., 0.1 torr) to obtain the title compound as a colorless oil.

$^1$H NMR (CDCl$_3$) δ 4.26–4.11 (q, 2H), 3.44–3.33 (m), 2.73–0.75 (m, 13H).

Step B: Preparation of Ethyl 2-amino-3-methyl-1-cyclohexene-1-carboxylate

Ammonia was bubbled through dioxane (60 mL) for 0.25 hour. The product of Step A (2.0 g, 10.9 mmol) was then added and the resulting solution was heated at 90° C. in a Fisher-Porter apparatus at 40 psi (275 kPa) overnight. Upon cooling, the solution was concentrated to give the title compound as a colorless oil in about 90% purity (the product of Step A constituted the remaining 10%).

$^1$H NMR (CDCl$_3$) δ 4.13 (q, 2H), 2.4–2.3 (m, 1H), 2.3–2.2 (m, 2H), 1.8–1.4 (m, 4H), 1.27 (t, 3H), 1.20 (d, 3H).

Step C: Preparation of 3-Bromo-N,N-dimethyl-1H-pyrazole-1-sulfonamide

To a solution of N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes. Then a solution of 1,2-dibromotetrachloroethane (90 g, 0.276 mol) in tetrahydrofuran (150 mL) was added dropwise while maintaining the temperature below −70° C. The reaction mixture turned to a clear orange color. After stirring for an additional 15 minutes, the −78° C. bath was removed and the reaction was quenched with water (600 mL). The reaction mixture was extracted with dichloromethane (4×), and the organic extracts were dried over magnesium sulfate and concentrated. The crude product was further purified by chromatography on silica gel using dichloromethane/hexane (50:50) as eluent to afford the title product as a clear colorless oil (57.04 g). $^1$H NMR (CDCl$_3$) δ 3.07 (d, 6H), 6.44 (m, 1H), 7.62 (m, 1H.

Step D: Preparation of 3-Bromopyrazole

To trifluoroacetic acid (70 mL) was slowly added the bromopyrazole product (57.04 g) from Step C. The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel eluted with dichloromethane/ethyl acetate (90:10) to afford an oil. The oil was taken up in dichloromethane, neutralized with aqueous sodium bicarbonate solution, extracted with dichloromethane (3×), dried over magnesium sulfate and concentrated to afford the title compound as a white solid (25.9 g), m.p. 61–64° C.

$^1$H NMR (CDCl$_3$) δ 6.37 (d, 1H), 7.59 (d, 1H), 12.4 (br s, 1H).

Step E: Preparation of 2-(3-Bromo-1H-pyrazol-1-yl)-3-chloropyridine

To a mixture of 2,3-dichloropyridine (27.4 g, 185 mmol) and 3-bromopyrazole (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hrs, filtered and washed with water (2×100 mL). The solid filter cake was taken up in dichloromethane and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hr. The solids were filtered, washed with hexane and dried to afford the title compound as an off-white powder (30.4 g) determined to be >94% pure by NMR. This material was used without further purification in Step F.

$^1$H NMR (CDCl$_3$) δ 6.52 (s, 1H), 7.30 (dd, 1H), 7.92 (d, 1H), 8.05 (s, 1H),

Step F: Preparation of 3-Bromo-1-(3-chloro-2-pyridinyl)-1H-pyrazole-5-carboxylic acid To a solution of the pyrazole product from Step E (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. After stirring for 15 minutes at −76° C., carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford the title product as a tan solid (27.7 g). (Product from another run following similar procedure melted at 200–201° C.)

$^1$H NMR (DMSO-d$_6$) δ 7.25 (s, 1H), 7.68 (dd, 1H), 8.24 (d, 1H), 8.56 (d, 1H).

Step G: Preparation of Ethyl 2-[[[3-bromo-1-(3-chloro-2-pyridinyl)-1H-pyrazol-5-yl]carbonyl]amino]-3-methyl-2-cyclohexene-1-carboxylate To a suspension of 3-bromo-1-(3-chloro-2-pyridinyl)-1H-pyrazole-5-carboxylic acid (i.e. the product of Step F) (1.0 g, 3.11 mmol) in dichloromethane (10 mL) was added dimethylformamide (20 μL) and oxalyl chloride (299 μL, 3.42 mmol). The mixture was stirred at ambient temperature until a clear solution resulted. The solution was then concentrated under reduced pressure and placed under high vacuum (0.1 torr) for 0.5 h. The residue was redissolved in acetone (5 mL) and added to a mixture of ethyl 2-amino-3-methyl-1-cyclohexene-1-carboxylate (i.e. the product of Step B) (570 mg, 3.11 mmol) and potassium carbonate (645 mg, 4.67 mmol) in acetone (10 mL). After stirring overnight at ambient temperature, water was added and the mixture was filtered through a column of celite and washed with dichloromethane. The eluent was concentrated and purified by silica gel column, chromatography (eluted with 60% then 80% ethyl ether in petroleum ether) to give the title compound as a white foam (0.2 g).

$^1$H NMR (CDCl$_3$) δ 8.47 (dd, 1H), 7.86 (dd, 1H), 7.52 (bs, 1H), 7.38 (s, 1H), 6.76 (s, 1H), 4.2–4.1 (m, 2H), 3.29 (bs, 1H), 2.1–2.0 (bm, 2H), 2.0–1.9 (m, 2H), 1.66–1.58 (m, 5H), 1.27 (t, 3H).

Step H: Preparation of 3-Bromo-1-(3-chloro-2-pyridinyl)-N-[6-methyl-2-[[(1-methylethyl)amino]carbonyl]-1-cyclohexen-1-yl]-1H-pyrazole-5-carboxamide Isopropyl amine (77 μL, 0.9 mmol) was added to a solution of trimethylaluminum (0.45 mL, 2M solution in hexanes, 0.9 mmol) in dichloromethane (10 mL). After stirring at ambient temperature for 1 h, ethyl 2-[[[3-bromo-1-(3-chloro-2-pyridinyl)-1H-pyrazol-5-yl]carbonyl]amino]-3-methyl-2-cyclohexene-1-carboxylate (i.e. the product of Step G) was added (425 mg, 0.9 mmol) in dichloromethane (5 mL) and the solution was heated at reflux for 24 hours and then overnight at ambient temperature. The reaction was quenched with water and the mixture was filtered through a column of celite and washed with dichloromethane. The eluent was concentrated and purified by silica gel column chromatography (eluted with 60% then 80% ethyl ether in petroleum ether then ethyl ether then ethyl acetate) to give the title compound, a compound of present invention, as a colorless oil (100 mg).

$^1$H NMR (CDCl$_3$) δ 8.59 (bs, 1H), 8.45 (dd, 1H), 7.88 (dd, 1H), 7.40 (dd, 1H), 7.12 (s, 1H), 6.24 (bd, 1H), 3.92 (m, 1H), 3.01 (bs,1H), 2.2–1.5 (m, 6H), 1.62 (s, 3H), 1.00 (d, 3H), 0.95 (d, 3H).

By the procedures described herein together with methods known in the art, the following compounds of Tables 1 to 10 can be prepared. The following abbreviations are used in the Tables which follow: t is tertiary, s is secondary, n is normal, i is iso, c is cyclo, Me is methyl, Et is ethyl, Pr is propyl, i-Pr is isopropyl, Bu is butyl and t-Bu is tertiary butyl.

TABLE 1

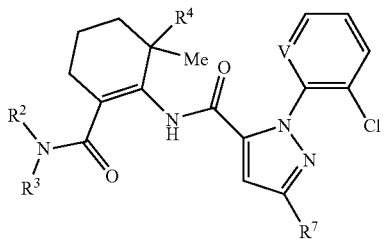

| V | R⁷ | R⁴ | R² | R³ | V | R⁷ | R⁴ | R² | R³ | V | R⁷ | R⁴ | R² | R³ |
|---|---|---|---|---|---|---|---|---|---|---|---|---|---|---|
| CH | Cl | H | H | Me | CH | Cl | Me | H | Me | CH | Cl | H | Me | Me |
| N | Cl | H | H | Me | N | Cl | Me | H | Me | N | Cl | H | Me | Me |
| CH | Br | H | H | Me | CH | Br | Me | H | Me | CH | Br | H | Me | Me |
| N | Br | H | H | Me | N | Br | Me | H | Me | CH | Cl | Me | H | t-Bu |
| CH | CF₃ | H | H | Me | CH | CF₃ | Me | H | Me | N | Cl | Me | H | t-Bu |
| N | CF₃ | H | H | Me | N | CF₃ | Me | H | Me | CH | Br | Me | H | t-Bu |
| CH | Cl | H | H | Et | CH | Cl | Me | H | Et | N | Br | Me | H | t-Bu |
| N | Cl | H | H | Et | N | Cl | Me | H | Et | CH | CF₃ | Me | H | t-Bu |
| CH | Br | H | H | Et | CH | Br | Me | H | Et | N | CF₃ | Me | H | t-Bu |
| N | Br | H | H | Et | N | Br | Me | H | Et | CH | Cl | H Me | Me | |
| CH | CF₃ | H | H | Et | CH | CF₃ | Me | H | Et | N | Cl | H | Me | Me |
| N | CF₃ | H | H | Et | N | CF₃ | Me | H | Et | CH | Br | Me | Me | Me |
| CH | Cl | H | H | i-Pr | CH | Cl | Me | H | i-Pr | N | Br | H | Me | Me |
| N | Cl | H | H | i-Pr | N | Cl | Me | H | i-Pr | CH | CF₃ | H | Me | Me |
| CH | Br | H | H | i-Pr | CH | Br | Me | H | i-Pr | N | CF₃ | H | Me | Me |
| N | Br | H | H | i-Pr | N | Br | Me | H | i-Pr | CH | Cl | Me | Me | Me |
| CH | CF₃ | H | H | i-Pr | CH | CF₃ | Me | H | i-Pr | N | Cl | Me | Me | Me |
| N | CF₃ | H | H | i-Pr | N | CF₃ | Me | H | i-Pr | CH | Br | Me | Me | Me |
| CH | Cl | H | H | t-Bu | N | Br | H | H | t-Bu | N | Br | Me | Me | Me |
| N | Cl | H | H | t-Bu | CH | CF₃ | H | H | t-Bu | CH | CF₃ | Me | Me | Me |
| CH | Br | H | H | t-Bu | N | CF₃ | H | H | t-Bu | N | CF₃ | Me | Me | Me |

TABLE 2

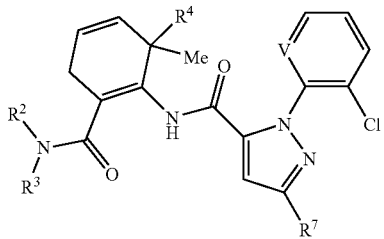

| V | R⁷ | R⁴ | R² | R³ | V | R⁷ | R⁴ | R² | R³ | V | R⁷ | R⁴ | R² | R³ |
|---|---|---|---|---|---|---|---|---|---|---|---|---|---|---|
| CH | Cl | H | H | Me | CH | Cl | Me | H | Me | CH | Cl | H | Me | Me |
| N | Cl | H | H | Me | N | Cl | Me | H | Me | N | Cl | H | Me | Me |
| CH | Br | H | H | Me | CH | Br | Me | H | Me | CH | Br | H | Me | Me |
| N | Br | H | H | Me | N | Br | Me | H | Me | CH | Cl | Me | H | t-Bu |
| CH | CF₃ | H | H | Me | CH | CF₃ | Me | H | Me | N | Cl | Me | H | t-Bu |
| N | CF₃ | H | H | Me | N | CF₃ | Me | H | Me | CH | Br | Me | H | t-Bu |
| CH | Cl | H | H | Et | CH | Cl | Me | H | Et | N | Br | Me | H | t-Bu |
| N | Cl | H | H | Et | N | Cl | Me | H | Et | CH | CF₃ | Me | H | t-Bu |
| CH | Br | H | H | Et | CH | Br | Me | H | Et | N | CF₃ | Me | H | t-Bu |
| N | Br | H | H | Et | N | Br | Me | H | Et | CH | Cl | H | Me | Me |
| CH | CF₃ | H | H | Et | CH | CF₃ | Me | H | Et | N | Cl | H | Me | Me |
| N | CF₃ | H | H | Et | N | CF₃ | Me | H | Et | CH | Br | H | Me | Me |
| CH | Cl | H | H | i-Pr | CH | Cl | Me | H | i-Pr | N | Br | H | Me | Me |
| N | Cl | H | H | i-Pr | N | Cl | Me | H | i-Pr | CH | CF₃ | H | Me | Me |
| CH | Br | H | H | i-Pr | CH | Br | Me | H | i-Pr | N | CF₃ | H | Me | Me |
| N | Br | H | H | i-Pr | N | Br | Me | H | i-Pr | CH | Cl | Me | Me | Me |
| CH | CF₃ | H | H | i-Pr | CH | CF₃ | Me | H | i-Pr | N | Cl | Me | Me | Me |
| N | CF₃ | H | H | i-Pr | N | CF₃ | Me | H | i-Pr | CH | Br | Me | Me | Me |
| CH | Cl | H | H | t-Bu | N | Br | H | H | t-Bu | N | Br | Me | Me | Me |
| N | Cl | H | H | t-Bu | CH | CF₃ | H | H | t-Bu | CH | CF₃ | Me | Me | Me |
| CH | Br | H | H | t-Bu | N | CF₃ | H | H | t-Bu | N | CF₃ | Me | Me | Me |

TABLE 3

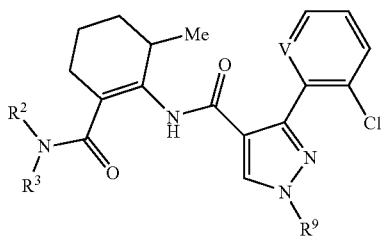

| R⁹ is CF₃ | | | R⁹ is CHF₂ | | | R⁹ is CH₂CF₃ | | | R⁹ is CF₂Br | | |
|---|---|---|---|---|---|---|---|---|---|---|---|
| V | R² | R³ | V | R² | R³ | V | R² | R³ | V | R² | R³ |
| CH | H | Me | CH | H | Me | CH | H | Me | CH | H | Me |
| N | H | Me | N | H | Me | N | H | Me | N | H | Me |
| CH | H | t-Bu | CH | H | t-Bu | CH | H | t-Bu | CH | H | t-Bu |
| N | H | t-Bu | N | H | t-Bu | N | H | t-Bu | N | H | t-Bu |
| CH | H | i-Pr | CH | H | i-Pr | CH | H | i-Pr | CH | H | i-Pr |
| N | H | i-Pr | N | H | i-Pr | N | H | i-Pr | N | H | i-Pr |
| CH | Me | Me | CH | Me | Me | CH | Me | Me | CH | Me | Me |
| N | Me | Me | N | Me | Me | N | Me | Me | N | Me | Me |

TABLE 4

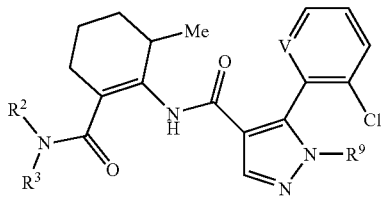

| R⁹ is CF₃ | | | R⁹ is CHF₂ | | | R⁹ is CH₂CF₃ | | | R⁹ is CF₂Br | | |
|---|---|---|---|---|---|---|---|---|---|---|---|
| V | R² | R³ | V | R² | R³ | V | R² | R³ | V | R² | R³ |
| CH | H | Me | CH | H | Me | CH | H | Me | CH | H | Me |
| N | H | Me | N | H | Me | N | H | Me | N | H | Me |
| CH | H | t-Bu | CH | H | t-Bu | CH | H | t-Bu | CH | H | t-Bu |
| N | H | t-Bu | N | H | t-Bu | N | H | t-Bu | N | H | t-Bu |
| CH | H | i-Pr | CH | H | i-Pr | CH | H | i-Pr | CH | H | i-Pr |
| N | H | i-Pr | N | H | i-Pr | N | H | i-Pr | N | H | i-Pr |
| CH | Me | Me | CH | Me | Me | CH | Me | Me | CH | Me | Me |
| N | Me | Me | N | Me | Me | N | Me | Me | N | Me | Me |

TABLE 5

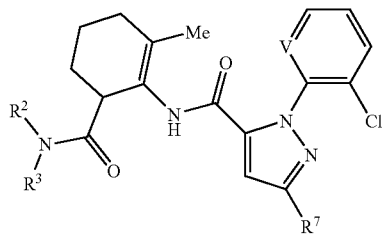

| V is CH | | | | | | V is N | | | | | |
|---|---|---|---|---|---|---|---|---|---|---|---|
| R⁷ is Cl | | R⁷ is Br | | R⁷ is CF₃ | | R⁷ is Cl | | R⁷ is Br | | R⁷ is CF₃ | |
| R² | R³ | R² | R³ | R² | R³ | R² | R³ | R² | R³ | R² | R³ |
| H | Me | H | Me | H | Me | H | Me | H | Me | H | Me |
| H | Et | H | Et | H | Et | H | Et | H | Et | H | Et |

TABLE 5-continued

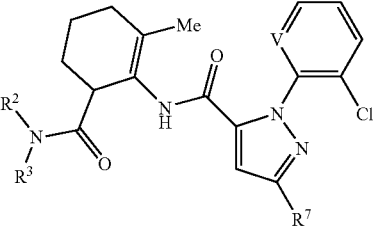

| V is CH | | | | | | V is N | | | | | |
|---|---|---|---|---|---|---|---|---|---|---|---|
| R⁷ is Cl | | R⁷ is Br | | R⁷ is CF₃ | | R⁷ is Cl | | R⁷ is Br | | R⁷ is CF₃ | |
| R² | R³ | R² | R³ | R² | R³ | R² | R³ | R² | R³ | R² | R³ |
| H | i-Pr | H | i-Pr | H | i-Pr | H | i-Pr | H | i-Pr | H | i-Pr |
| H | t-Bu | H | t-Bu | H | t-Bu | H | t-Bu | H | t-Bu | H | t-Bu |
| Me | Me | Me | Me | Me | Me | Me | Me | Me | Me | Me | Me |

TABLE 6

| R⁹ is CF₃ | | | R⁹ is CHF₂ | | | R⁹ is CH₂CF₃ | | | R⁹ is CF₂Br | | |
|---|---|---|---|---|---|---|---|---|---|---|---|
| V | R² | R³ | V | R² | R³ | V | R² | R³ | V | R² | R³ |
| CH | H | Me | CH | H | Me | CH | H | Me | CH | H | Me |
| N | H | Me | N | H | Me | N | H | Me | N | H | Me |
| CH | H | t-Bu | CH | H | t-Bu | CH | H | t-Bu | CH | H | t-Bu |
| N | H | t-Bu | N | H | t-Bu | N | H | t-Bu | N | H | t-Bu |
| CH | H | i-Pr | CH | H | i-Pr | CH | H | i-Pr | CH | H | i-Pr |
| N | H | i-Pr | N | H | i-Pr | N | H | i-Pr | N | H | i-Pr |
| CH | Me | Me | CH | Me | Me | CH | Me | Me | CH | Me | Me |
| N | Me | Me | N | Me | Me | N | Me | Me | N | Me | Me |

TABLE 7

| R⁹ is CF₃ | | | R⁹ is CHF₂ | | | R⁹ is CH₂CF₃ | | | R⁹ is CF₂Br | | |
|---|---|---|---|---|---|---|---|---|---|---|---|
| V | R² | R³ | V | R² | R³ | V | R² | R³ | V | R² | R³ |
| CH | H | Me | CH | H | Me | CH | H | Me | CH | H | Me |
| N | H | Me | N | H | Me | N | H | Me | N | H | Me |
| CH | H | t-Bu | CH | H | t-Bu | CH | H | t-Bu | CH | H | t-Bu |
| N | H | t-Bu | N | H | t-Bu | N | H | t-Bu | N | H | t-Bu |
| CH | H | i-Pr | CH | H | i-Pr | CH | H | i-Pr | CH | H | i-Pr |
| N | H | i-Pr | N | H | i-Pr | N | H | i-Pr | N | H | i-Pr |
| CH | Me | Me | CH | Me | Me | CH | Me | Me | CH | Me | Me |
| N | Me | Me | N | Me | Me | N | Me | Me | N | Me | Me |

TABLE 8

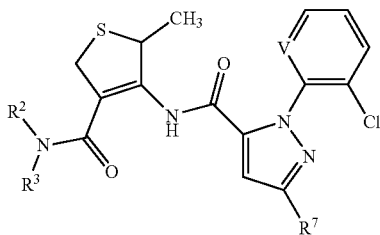

| V is CH | | | | | | V is N | | | | | |
|---|---|---|---|---|---|---|---|---|---|---|---|
| $R^7$ is Cl | | $R^7$ is Br | | $R^7$ is CF$_3$ | | $R^7$ is Cl | | $R^7$ is Br | | $R^7$ is CF$_3$ | |
| $R^2$ | $R^3$ | $R^2$ | $R^3$ | $R^2$ | $R^3$ | $R^2$ | $R^3$ | $R^2$ | $R^3$ | $R^2$ | $R^3$ |
| H | Me | H | Me | H | Me | H | Me | H | Me | H | Me |
| H | Et | H | Et | H | Et | H | Et | H | Et | H | Et |
| H | i-Pr | H | i-Pr | H | i-Pr | H | i-Pr | H | i-Pr | H | i-Pr |
| H | t-Bu | H | t-Bu | H | t-Bu | H | t-Bu | H | t-Bu | H | t-Bu |
| Me | Me | Me | Me | Me | Me | Me | Me | Me | Me | Me | Me |

TABLE 9

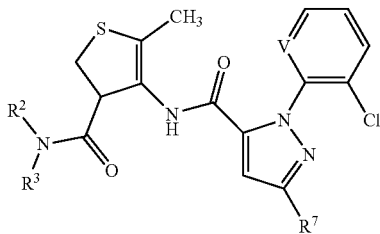

| V is CH | | | | | | V is N | | | | | |
|---|---|---|---|---|---|---|---|---|---|---|---|
| $R^7$ is Cl | | $R^7$ is Br | | $R^7$ is CF$_3$ | | $R^7$ is Cl | | $R^7$ is Br | | $R^7$ is CF$_3$ | |
| $R^2$ | $R^3$ | $R^2$ | $R^3$ | $R^2$ | $R^3$ | $R^2$ | $R^3$ | $R^2$ | $R^3$ | $R^2$ | $R^3$ |
| H | Me | H | Me | H | Me | H | Me | H | Me | H | Me |
| H | Et | H | Et | H | Et | H | Et | H | Et | H | Et |
| H | i-Pr | H | i-Pr | H | i-Pr | H | i-Pr | H | i-Pr | H | i-Pr |
| H | t-Bu | H | t-Bu | H | t-Bu | H | t-Bu | H | t-Bu | H | t-Bu |
| Me | Me | Me | Me | Me | Me | Me | Me | Me | Me | Me | Me |

TABLE 10

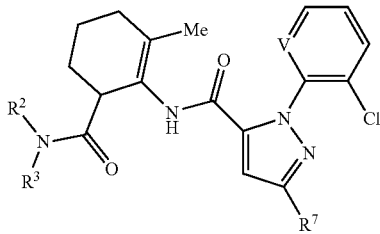

| V is CH | | | | | | V is N | | | | | |
|---|---|---|---|---|---|---|---|---|---|---|---|
| $R^7$ is Cl | | $R^7$ is Br | | $R^7$ is CF$_3$ | | $R^7$ is Cl | | $R^7$ is Br | | $R^7$ is CF$_3$ | |
| $R^2$ | $R^3$ | $R^2$ | $R^3$ | $R^2$ | $R^3$ | $R^2$ | $R^3$ | $R^2$ | $R^3$ | $R^2$ | $R^3$ |
| H | Me | H | Me | H | Me | H | Me | H | Me | H | Me |
| H | Et | H | Et | H | Et | H | Et | H | Et | H | Et |
| H | i-Pr | H | i-Pr | H | i-Pr | H | i-Pr | H | i-Pr | H | i-Pr |

TABLE 10-continued

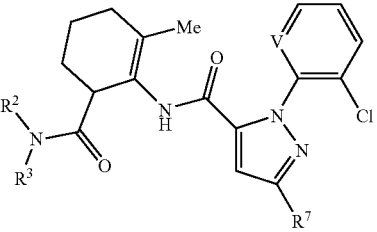

| V is CH | | | | | | V is N | | | | | |
|---|---|---|---|---|---|---|---|---|---|---|---|
| $R^7$ is Cl | | $R^7$ is Br | | $R^7$ is $CF_3$ | | $R^7$ is Cl | | $R^7$ is Br | | $R^7$ is $CF_3$ | |
| $R^2$ | $R^3$ | $R^2$ | $R^3$ | $R^2$ | $R^3$ | $R^2$ | $R^3$ | $R^2$ | $R^3$ | $R^2$ | $R^3$ |
| H | t-Bu | H | t-Bu | H | t-Bu | H | t-Bu | H | t-Bu | H | t-Bu |
| Me | Me | Me | Me | Me | Me | Me | Me | Me | Me | Me | Me |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed, McGraw-Hill, New York, 1963, pages 8–57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120–133. See also U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 1 | 10.0% |
| attapulgite granules (low volatile matter, 0.71/0.30 mm; U.S.S. No. 25–50 sieves) | 90.0%. |

EXAMPLE C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 1 | 20.0% |
| blend of oil soluble sulfonates and polyoxyethylene ethers | 10.0% |
| isophorone | 70.0%. |

EXAMPLE E

Granule

| | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and nonagronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition it includes: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linneus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Activity also includes members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and aninal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trchoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Thoza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can fulrther comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyflutrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, ediferphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi.

A general reference for these agricultural protectants is *The Pesticide Manual,* 12*th Edition,* C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, seed coatings, microencapsulations, systemic uptake, baits, eartags, boluses, foggers, fumigants, aerosols, dusts and many others.

The compounds of this invention can be incorporated into baits that are consumed by the invertebrates or within devices such as traps and the like. Granules or baits comprising between 0.01–5% active ingredient, 0.05–10% moisture retaining agent(s) and 40–99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrates, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter maybe required. One skilled in the art can easily determine the biologically effective amount necessary for the desired level of invertebrate pest control.

The following Tests in the Biological Examples of the Invention demonstrate the efficacy of methods of the invention for protecting plants from specific arthropod pests. "Control efficacy" represents inhibition of arthropod development (including mortality) that causes significantly reduced feeding. The pest control protection afforded by the compounds is not limited, however, to these species. See Index Table A for compound descriptions. The abbreviation "Ex." stands for "Example" and is followed by a number indicating in which example the compound is prepared.

INDEX TABLE A

| Compound | | m.p. (° C.) |
|---|---|---|
| 1 (Ex. 1) | [structure] | * |
| 2 (Ex. 2) | [structure] | * |

*See Index Table B for $^1$H NMR data.

INDEX TABLE B

| Cmpd No. | $^1$H NMR Data (CDCl$_3$ solution unless indicated otherwise)$^a$ |
|---|---|
| 1 | 8.81 (bs, 1H), (dd, 1H), 7.93 (dd, 1H), 7.47 (dd, 1H), 7.42 (s, 1H), 6.16 (bd, 1H), 4.03-3.84 (m, 2H), 3.40 (m, 1H), 3.38 (m, 1H), 1.87 (d, 3H), 0.99 (d 3H), 0.95 (d, 3H). |
| 2 | 8.59 (bs, 1H), 8.45 (dd, 1H), 7.88 (dd, 1H), 7.40 (dd, 1H), 7.12 (s, 1H), 6.24 (bd, 1H), 3.92 (m, 1H), 3.01 (bs, 1H), 2.2-1.5 (m, 6H), 1.62 (s, 3H), 1.00 (d, 3H), 0.95 (d, 3H). |

$^a$$^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

For evaluating control of diamondback moth (*Plutella xylostella*) the test unit consisted of a small open container with a 12–14-day-old radish plant inside. This was pre-infested (using a core sampler) with 10–15 neonate larvae on a piece of insect diet.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co,) positioned 1.27 cm (0.5 inches) above the top of each test unit. All experimental compounds in this screen were sprayed at 250 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (10% or less feeding damage): 1 and 2.

Test B

For evaluating control of tobacco budworm (*Heliothis virescens*) the test unit consisted of a small open container with a 6–7 day old cotton plant inside. This was pre-infested with 8 2-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided very good levels of plant protection (20% or less feeding damage) at the rates tested: 1 and 2.

Test C

For evaluating control of beet armyworm (*Spodoptera exigua*) the test unit consisted of a small open container with a 4–5-day-old corn (maize) plant inside. This was pre-infested with 10–15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided very good levels of plant protection (20% or less feeding damage) at the rates tested: 1.

What is claimed is:

1. A compound of Formula I, its N-oxide or suitable salt thereof

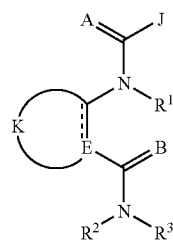

I wherein

A and B are O;

E is C;

J is pyrazole optionally substituted with 1 to 4 $R^5$;

K is taken together with the two contiguous linking atoms to form a 6-membered nonaromatic carbocyclic ring optionally substituted with 1 to 4 $R^4$;

$R^1$ and $R^2$ are each independently H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^3$ is H; $C_1$–$C_6$ alkyl, $C_2$–$C_6$ alkenyl, $C_2$–$C_6$ alkynyl, $C_3$–$C_6$ cycloalkyl, each optionally substituted with 1 to 5 substituents selected from the group consisting of halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, phenyl and phenoxy each phenyl or phenoxy optionally substituted with one to three substituents independently selected from $R^6$;

each $R^4$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfanyl, $C_1$–$C_4$ alkylamino, $C_2$–$C_8$ dialkylamino, $C_3$–$C_6$ cycloalkylamino, $C_1$–$C_4$ alkoxyalkyl, $C_1$–$C_4$ hydroxyalkyl, $C(O)R^{10}$, $CO_2R^{10}$, $C(O)NR^{10}R^{11}$, $NR^{10}R^{11}$, $N(R^{11})CO_2R^{10}$ or $C_3$–$C_6$ trialkylsilyl; or each $R^4$ is independently a phenyl, benzyl, phenoxy or 5 or 6-membered heteroaromatic ring, each ring optionally substituted with one to three substituents independently selected from $R^6$;

each $R^5$ is independently $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylsulfonyloxy, $C_1$–$C_4$ haloalkylthio, $C_1$–$C_4$ haloalkylsulfinyl, $C_1$–$C_4$ haloalkylsulfonyl, $C_2$–$C_4$ haloalkylsulfonyloxy, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring or ring system optionally substituted with one to three substituents independently selected from $R^6$; or two $R^5$ groups when attached to adjacent carbon atoms can be taken together as —$OCF_2O$—, —$CF_2CF_2O$—, or —$OCF_2CF_2O$—;

each $R^6$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

each $R^{10}$ is independently H, $C_1$–$C_4$ alkyl or $C_1$–$C_4$ haloalkyl; and each $R^{11}$ is independently H or $C_1$–$C_4$ alkyl.

2. The compound of claim 1 wherein each $R^4$ is independently $C_1$–$C_4$ alkyl, $C_1$–$C_4$ haloalkyl, halogen, CN, $NO_2$ or $C_1$–$C_4$ Image Page 5 alkoxy, and one $R^4$ group is attached to the K ring at the carbon adjacent to either the $NR^1C(=A)J$ moiety or the $C(=B)NR^2R^3$ moiety; and each $R^5$ is independently $C_1$–$C_4$ alkyl, $C_1$–$C_4$ haloalkyl, halogen, CN, $NO_2$, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl;

each $R^5$ is independently a phenyl or a 5- or 6-membered heteroaromatic ring, each ring optionally substituted with one to three substituents independently selected from $R^6$.

3. The compound of claim 2 wherein

J substituted with 1 to 3 $R^5$ is selected from the group consisting of J-6, J-7, and J-10

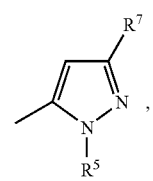

J-6

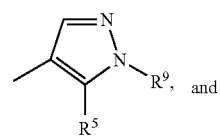

J-7, and

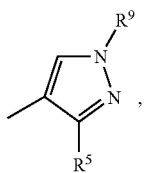

J-10

$R^5$ is $C_1$–$C_4$ alkyl, $C_1$–$C_4$ haloalkyl, or

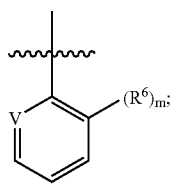

V is N, CH, CF, CCl, CBr or CI;
$R^6$ is $C_1$–$C_6$ alkyl, $C_1$–$C_6$ cycloalkyl, $C_1$–$C_4$ haloalkyl, halogen, CN, $C_1$–$C_4$ alkoxy, $C_1$–$C_4$ haloalkoxy or $C_1$–$C_4$ haloalkylthio;
each $R^7$ is independently H, $C_1$–$C_6$ alkyl, $C_3$–$C_6$ cycloalkyl, $C_1$–$C_4$ haloalkyl, halogen, CN, $C_1$–$C_4$ alkoxy, $C_1$–$C_4$ haloalkoxy or $C_1$–$C_4$ haloalkylthio;
each $R^9$ is independently H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl; provided $R^7$ and $R^9$ are not both H; and
m is 0 or 1.

4. The compound of claim 3 wherein V is N.

5. The compound of claim 3 wherein V is CH, CF, CCl or CBr.

6. The compound of claim 4 or claim 5 wherein $R^1$ and $R^2$ are both H;

$R^3$ is $C_1$–$C_4$ alkyl optionally substituted with 1 to 5 substituents independently selected from the group consisting of halogen, CN, $OCH_3$ and $S(O)_pCH_3$;
each $R^4$ is independently $CH_3$, $CF_3$, CN or halogen, and one group is attached to the K ring at the carbon adjacent to the $NR^1C(=A)J$ moiety;
$R^6$ is $C_1$–$C_4$ alkyl, $C_1$–$C_4$ haloalkyl, halogen or CN;
$R^7$ is H, $CH_3$, $CF_3$, $OCHF_2$ or halogen;
p is 0, 1 or 2; and
m is 1.

7. The compound of claim 6 wherein $R^3$ is $C_1$–$C_4$ alkyl; each $R^4$ group is independently $CH_3$, Cl, Br or I; and an optionally second $R^4$ is F, Cl, Br, I, CN or $CF_3$.

8. The compound of claim 7 wherein J is J-6; $R^6$ is halogen; and $R^7$ is halogen or $CF_3$.

9. The compound of claim 8 wherein V is N; $R^3$ is methyl, ethyl, isopropyl or tertiary butyl and $R^7$ is Br, CI or $CF_3$.

10. The compound of claim 7 wherein J is J-7; $R^6$ is halogen; and $R^9$ is $CF_3$, $CHF_2$, $CH_2CF_3$ or $CF_2CHF_2$.

11. The compound of claim 7 wherein J is J-10; $R^6$ is halogen; and $R^9$ is $CF_3$, $CHF_2$, $CH_2CF_3$ or $CF_2CHF_2$.

12. The compound of claim 8 which is
3-bromo-1-(3-chloro-2-pyridinyl)-N-[2-methyl-6-[[(1-methylethyl)amino]carbonyl]-1-cyclohexen-1-yl]-1H-pyrazole-5-carboxamide.

13. A method for controlling an invertebrate pest comprising contacting the invertebrate pest or its environment with a biologically effective amount of a compound of claim 1.

14. A composition for controlling an invertebrate pest comprising a biologically effective amount of a compound of claim 1 and at least one additional component selected from the group consisting of surfactants, solid diluents and liquid diluents, said composition optionally further comprising an effective amount of at least one additional biologically active compound or agent.

* * * * *